US009422341B2

(12) United States Patent
Kirihata et al.

(10) Patent No.: US 9,422,341 B2

(45) Date of Patent: Aug. 23, 2016

(54) METHOD FOR PRODUCING CEREULIDE AND DERIVATIVE THEREOF, INTERMEDIATE FOR PRODUCTION OF CEREULIDE, AND CEREULIDE DERIVATIVE

(71) Applicants: Stella Pharma Corporation, Osaka (JP); Osaka Prefecture University Public Corporation, Osaka (JP)

(72) Inventors: Mitsunori Kirihata, Osaka (JP); Kohki Uehara, Osaka (JP)

(73) Assignees: Stella Pharma Corporation, Osaka (JP); Osaka Prefecture University Public Corporation, Osaka (JP)

( * ) Notice: Subject to any disclaimer, the term of this patent is extended or adjusted under 35 U.S.C. 154(b) by 0 days.

(21) Appl. No.: 14/377,748

(22) PCT Filed: Feb. 7, 2013

(86) PCT No.: PCT/JP2013/052870

§ 371 (c)(1),
(2) Date: Aug. 8, 2014

(87) PCT Pub. No.: WO2013/118823

PCT Pub. Date: Aug. 15, 2013

(65) Prior Publication Data

US 2015/0183831 A1 Jul. 2, 2015

(30) Foreign Application Priority Data

Feb. 8, 2012 (JP) ................................ 2012-024722

(51) Int. Cl.

| | |
|---|---|
| ***C07K 11/02*** | (2006.01) |
| ***C07C 229/08*** | (2006.01) |
| ***C07C 235/12*** | (2006.01) |
| ***C07K 14/32*** | (2006.01) |
| ***C07C 229/24*** | (2006.01) |
| ***C07D 273/00*** | (2006.01) |
| ***C07C 237/12*** | (2006.01) |
| ***C07K 11/00*** | (2006.01) |

(52) U.S. Cl.

CPC ............ *C07K 11/02* (2013.01); *C07C 229/08* (2013.01); *C07C 229/24* (2013.01); *C07C 235/12* (2013.01); *C07C 237/12* (2013.01); *C07D 273/00* (2013.01); *C07K 11/00* (2013.01); *C07K 14/32* (2013.01)

(58) Field of Classification Search

CPC .................................................... C07K 11/02

USPC ................................................ 530/323, 317

See application file for complete search history.

(56) References Cited

FOREIGN PATENT DOCUMENTS

| | | |
|---|---|---|
| JP | 2006006256 A | 1/2006 |
| WO | 03097821 | 11/2003 |

OTHER PUBLICATIONS

Biesta-Peter, E.G., et al; Quantification of the Enetic Toxin Cereulide in Food Products by Liquid Chomatopraphy-Mass Spectrometry Using Synthetic Cereulide as a Standard; vol. 76, No. 22, pp. 7466-7472.

Japanese Office Action mailed Jun. 30, 2015 during examination of JP Appl. No. 2013-557569.

Extended European Search Report from related European Patent Application No. 13746354.3, dated Oct. 21, 2015, 6 pages.

Kamata, Yoichi, et al.; Study Abstract, Mar. 2011, pp. 11-36, with partial English translation.

Isobe, Minoru et al.; Synthesis and Activity of Cereulide a Cyclic Dodecadepsipeptide lonophore as Emetic Toxin from Bacillus cereus; vol. 5., No. 23; (1995), pp. 2855-2858.

*Primary Examiner* — David Lukton

(74) *Attorney, Agent, or Firm* — Norton Rose Fulbright US LLP

(57) ABSTRACT

The purpose of the present invention is to provide a novel method for producing cereulide and a derivative thereof; an intermediate for cereulide; and a novel cereulide derivative. A novel didepsipeptide, a novel tetradepsipeptide, a novel octadepsipeptide and a novel dodecadepsipeptide are prepared. A linear precursor of cereulide or a derivative thereof, which is composed of any one of the novel depsipeptides, is cyclized by forming an intramolecular amide bond.

3 Claims, 2 Drawing Sheets

METHOD FOR PRODUCING CEREULIDE AND DERIVATIVE THEREOF, INTERMEDIATE FOR PRODUCTION OF CEREULIDE, AND CEREULIDE DERIVATIVE

CROSS-REFERENCE TO RELATED APPLICATIONS

This application is a national phase application under 35 U.S.C. §371 that claims priority to PCT Application No. PCT/JP2013/052870 filed on Feb. 7, 2013, which claims the benefit of Japanese Application No. 2012-024722 filed Feb. 8, 2012, all of which are incorporated herein by reference in their entireties.

TECHNICAL FIELD

The present invention relates to a method for producing cereulide and a derivative thereof. The present invention also relates to an intermediate for production of cereulide and a cereulide derivative.

BACKGROUND OF THE INVENTION

*Bacillus cereus* that lives in the soil propagates in starch-based foods such as rice, pilaf and spaghetti, and produces cereulide that induces an emetic action on an animal such as human. It is also known that not all *Bacillus cereus* species produce cereulide, but only *Bacillus cereus* species which acquire a cereulide synthetic gene produce this toxic substance.

Currently, when food poisoning by cereulide is suspected, a method for identifying cereulide in an extract of the food by HPLC or LC/MS is carried out. There is also a method for carrying out bioassay using cells, using a vacuolating action of cereulide as an index.

It is known that such cereulide has high heat resistance, acid resistance, and resistance to digestive enzymes, is not deactivated in the process of cooking and digestion, and acts on the small intestine nervous system to induce vomiting phenomenon. Furthermore, liver damage, mitochondrial toxicity, induction of alteration of cellular morphology, apoptosis induction and the like are reported, but researches of molecular mechanism of the vomiting phenomenon or other toxicity at a molecular level have not made any progress.

For the determination of food poisoning, methods by detection of a synthetic enzyme gene in a specimen (Patent Documents 1 and 2) are also suggested.

However, development of a simple analysis method, not a method requiring an expensive analytical instrument and skilled technique, is desirable.

For qualitative or quantitative analysis for determining food poisoning due to cereulide, as well as toxicity evaluation or elucidation of the mechanism at a cellular or molecular level, a pure cereulide reference standard is often required.

Currently commercially available cereulide is extracted from a culture solution of *Bacillus cereus*, and is available as a methanol solution of cereulide.

As a method for obtaining such cereulide, methods for synthesizing cereulide and a derivative thereof are also suggested (Non-Patent Documents 1 and 2).

PRIOR ART

Patent Documents

Patent Document 1: WO 3/097821
Patent Document 2: JP 2006-6256

PRIOR ART

Non-Patent Documents

Non-Patent Document 1: Bioorganic & Medicinal Chemistry Letters, Vol. 5, No. 23, 2855-2858 (1995)
Non-Patent Document 2: Synthesis 2009, No. 13, 2184-2204

BRIEF SUMMARY OF THE INVENTION

Currently commercially available cereulide is very expensive, and is derived from a culture solution, thus the purity of the cereulide is not so high. It has been desirable to easily produce highly pure cereulide.

Thus, an object of the present invention is to provide a method for producing cereulide and a derivative thereof, and a cereulide derivative.

The present inventors have intensively studied, and found that the object can be achieved by the method for producing cereulide and a derivative thereof, an intermediate for production of cereulide, and a cereulide derivative, whereby the present invention is accomplished.

More specifically, the present invention relates to cereulide or a precursor of a derivative thereof, selected from the group consisting of the following formulae:

[Formula 1]

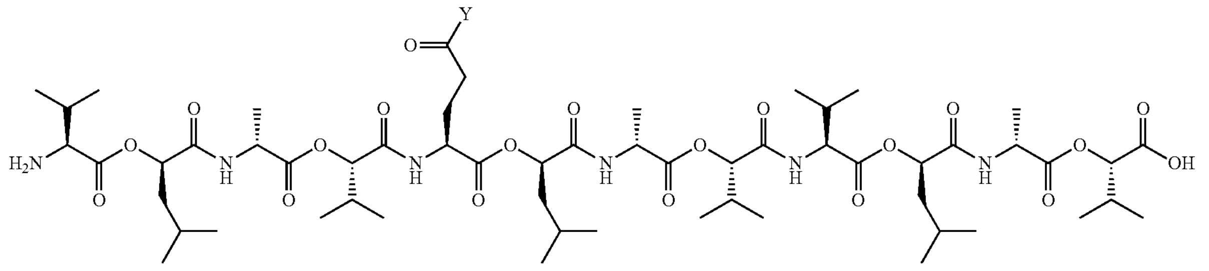

-continued

[Formula 2]

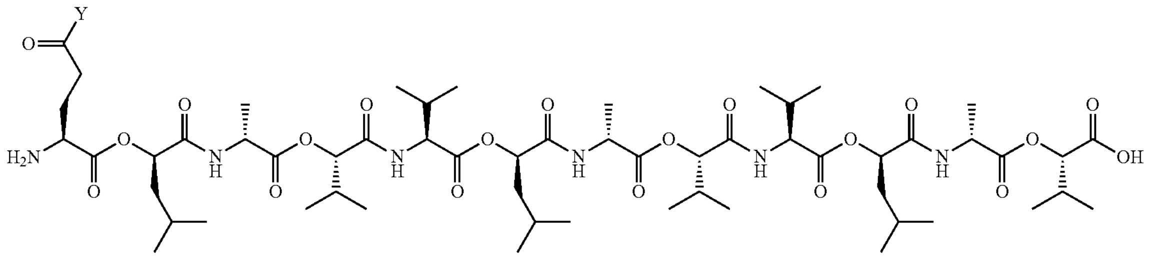

and

[Formula 3]

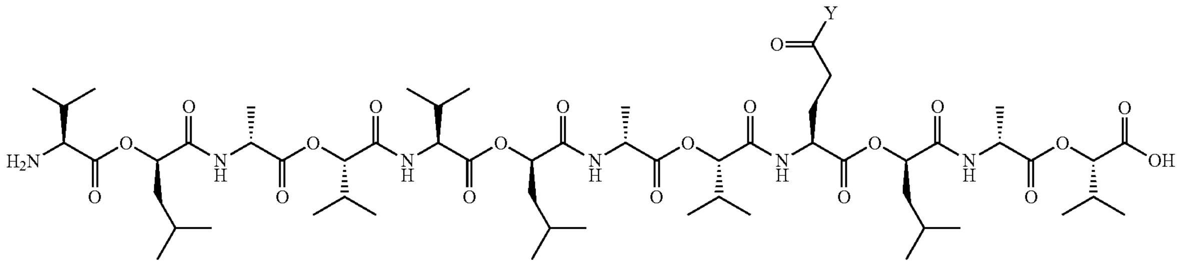

wherein Y represents OH or $NH(CH_2)_5COOH$.

The present invention further relates to a didepsipeptide represented by

[Formula 4]

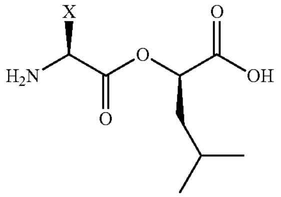

Or

[Formula 5]

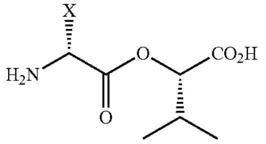

wherein X represents isopropyl, $(CH_2)_2COOH$ or $(CH_2)_2CONH(CH_2)_5COOH$.

The present invention further relates to a depsipeptide as shown below

[Formula 6]

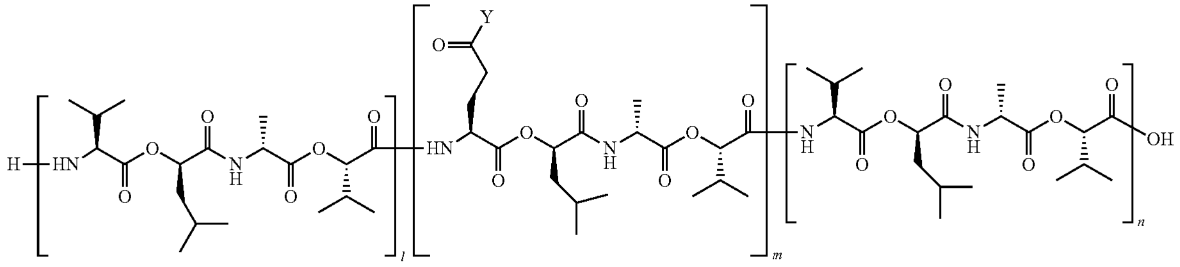

wherein 1 is an integer of 0 to 2, n is an integer of 0 to 2, and m is an integer of 0 or 1, wherein 1, m and n are not simultaneously 0, and 1+m+n is 2 or less.

The present invention further relates to a method for producing cereulide or a derivative thereof represented by

[Formula 7]

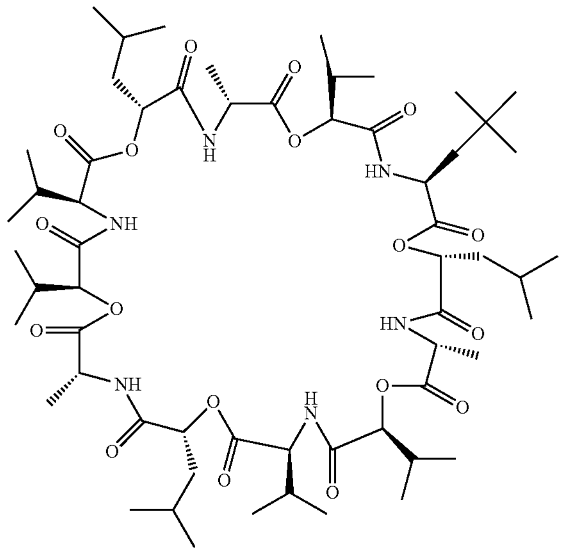

wherein X represents isopropyl, $(CH_2)_2COOH$ or $(CH_2)_2CONH(CH_2)_5COOH$, comprising a cyclization reaction by formation of an intramolecular amide bond of the precursor of cereulide or a derivative thereof.

In the production method, it is preferred to further comprise a step of preparing the didepsipeptide.

In the production method, it is preferred to further comprise a step of preparing the depsipeptide of

[Formula 8]

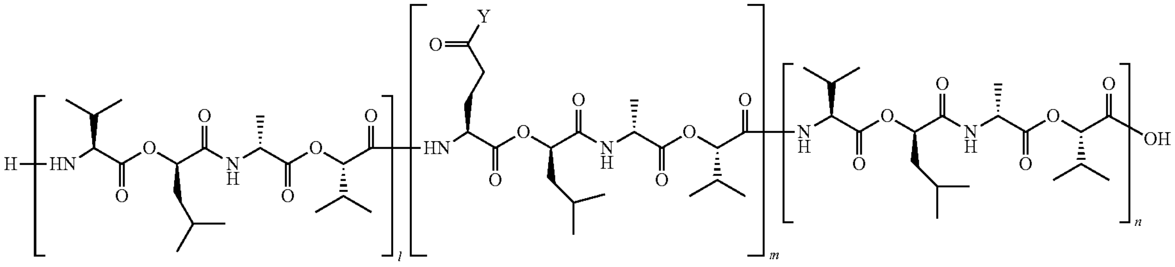

The present invention further relates to a cereulide derivative represented by the following formula:

[Formula 9]

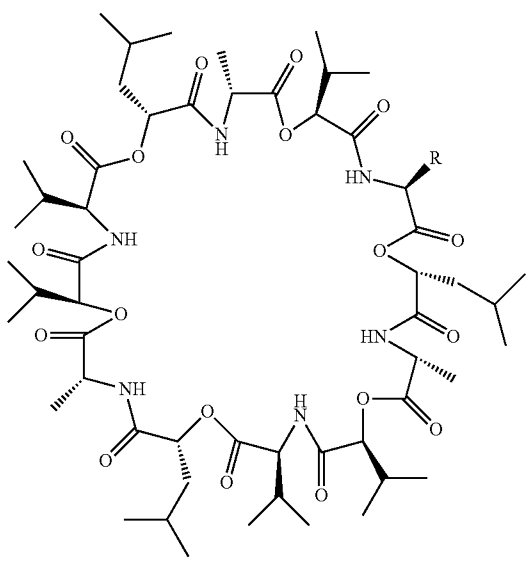

wherein R represents $(CH_2)_2COOH$ or $(CH_2)_2CONH(CH_2)_5COOH$.

Effect of the Invention

According to the method for producing cereulide and a derivative thereof of the present invention, highly pure cereulide or a derivative thereof can be easily obtained. Furthermore, the cereulide derivative of the present invention is useful for antibody preparation for detecting cereulide.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
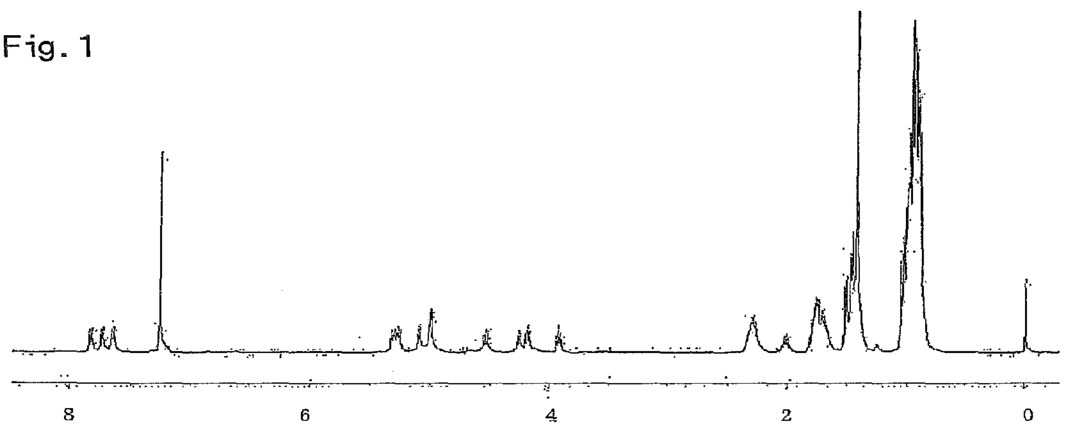
FIG. 1 is a $^1$H-NMR ($CDCl_3$) spectrum of the octadepsipeptide of the present invention.

Cereulide is a 36-membered macrocyclic compound (macrolide) in which six amino acids and six hydroxy acids are alternatively linked by an amide bond and an ester bond, and can also be called as cyclododecadepsipeptide. Cereulide has the structure as follows, that is constituted of two types of amino acids, L-valine (L-Val) and D-alanine (D-Ala) and two types of α-hydroxy acids, D-leucine acid (D-O-Leu) and L-valine acid (L-O-Val).

[Formula 10]

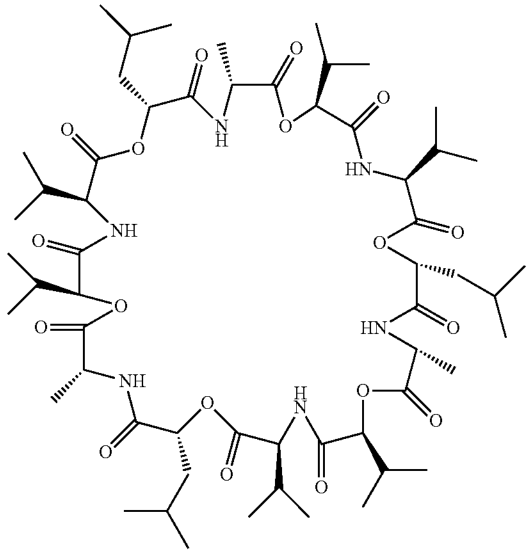

In many cases, cereulide functions as an ionophore of $K^+$, $Na^+$, or $NH_4^+$. Such a capturing action is considered as a cause of bioactivities.

The inventors have considered that the step of cyclizing a linear precursor to construct a 36-membered ring structure is the most important key stage in the total synthesis of cereulide, and have focused on that the method by formation of an ester bond is conventionally adopted for achieving this cyclization reaction. Regarding cereulide and a derivative, all the conventionally known synthetic methods include a cyclization step as shown in the following schematic view.

[Formula 11]

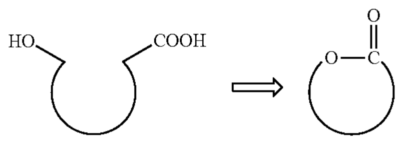

Precursor Cereulide

In the present invention, a tetradepsipeptide L-Val-D-O-Leu-D-Ala-L-O-Val is focused as a repeating structure unit of cereulide. More specifically, cereulide is a macrolide cyclized by linking three of the repeating structure units, and can also be described as $(\text{L-Val-D-O-Leu-D-Ala-L-O-Val})_3$.

The present invention relates to a novel production method including macrocyclic construction by amide bond formation as a key reaction, unlike a conventional method. The starting materials in the production method of the present invention are all commercially available, and two hydroxy acids, i.e., D-leucine acid (D-O-Leu) and L-valine acid (L-O-Val), can be prepared from commercially available D-leucine and L-valine, by a method known in the literature, and used in the following fragment synthesis.

Further, in the present invention, taking note on the problem that, in the depsipeptide synthesis, the longer the peptide chain is, the larger the steric hindrance is, whereby the solubility in an organic solvent is reduced to cause reduction in the reaction yield. Thus, in order to avoid such a problem, a method of first synthesizing a tetradepsipeptide repeating structural unit, followed by binding two of the structural units to obtain an octadepsipeptide (2× structural unit), thereafter further binding the octadepsipeptide with a tetradepsipeptide to prepare a linear dodecadepsipeptide of three structural units (precursor) and cyclizing the dodecadepsipeptide is adopted.

The intramolecular cyclization reaction of a precursor by amide bond construction in the present invention can also be carried out by changing various reaction conditions such as a condensing agent, a solvent and the temperature, and can also be optimized for realizing a high yield.

According to the method of the present invention, synthesis of cereulide and a derivative thereof can be sought in commercially available raw materials (amino acid). More specifically, it is possible to synthesize cereulide using L-valine, D-leucine and D-alanine, and synthesize a derivative by adding L-glutamic acid and 6-aminohexanoic acid to these materials.

Hereinbelow, the method of the present invention will be described in detail by each synthetic stage of the fragment. As a protective group used in the production, for example, protective groups described in "Protective Groups in Organic Synthesis (1999)" from WILEY-Interscience publication are properly used.

First, as the amino acid required for synthesis, L-valine with any protective group attached thereto can be used in the synthesis, and a commercially available product with a protective group attached thereto can also be used as it is. Examples of the commercially available product include Boc-L-valine protected with a tert-butoxycarbonyl group manufactured by Tokyo Chemical Industry Co., Ltd.

Next, D-leucine acid and L-valine acid can be respectively synthesized from D-leucine and L-valine. Hydroxy acids such as D-leucine acid and L-valine acid can be used in any method as long as it is a method that can convert an amino group of D-leucine acid and L-valine acid into a hydroxyl group.

A representative example is a method of reacting D-leucine or L-valine with a nitrite. It is preferred that D-leucine or L-valine be dissolved in a strong acid such as sulfuric acid or hydrochloric acid, prior to this reaction, and used.

Furthermore, it is also possible to attach a protective group to the hydroxy acid obtained as described above, in preparation for the next reaction. As the protective group, a benzyl group and the like are preferably used.

[Formula 12]

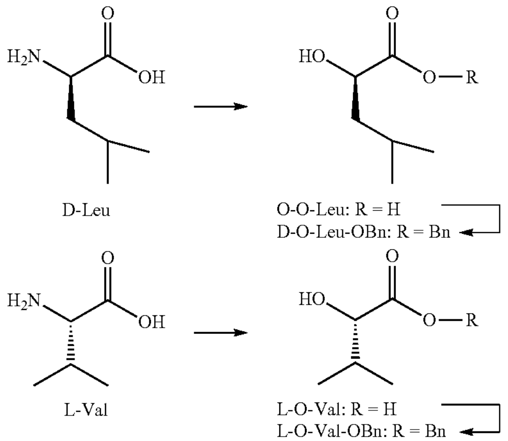

Similarly, a protective group can also be added to D-alanine to prepare for the next reaction.

Next, a didepsipeptide is synthesized using the amino acid and hydroxy acid obtained as described above.

A didepsipeptide may be synthesized under any condition as long as it is a condition that can achieve esterification by a dehydration reaction. Particularly preferred is a reaction carried out by adding a strong base such as dimethylaminopyridine and dicyclohexylcarbodiimide to a solvent such as a dichloromethane solution, but the synthesis condition is not limited thereto.

It is preferred to bind L-valine to D-leucine acid, then remove a group protecting the carboxyl group and use it in the subsequent tetradepsipeptide synthesis. Meanwhile, it is possible to bind D-alanine to D-valine acid, then remove the group protecting the amino group and use it in the subsequent tetradepsipeptide synthesis.

[Formula 13]

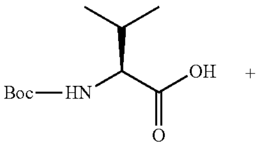

1: Boc-L-Val

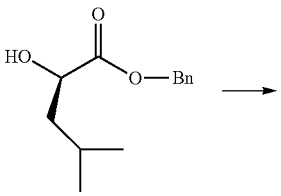

4: D-O-Leu-OBn

-continued

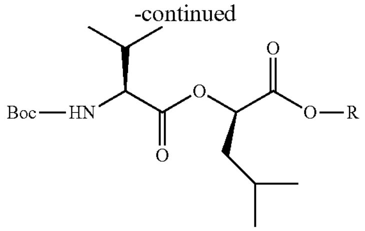

7: R = Bn
8: R = H

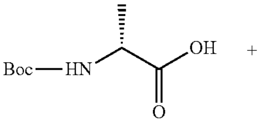

2: Boc-D-Ala

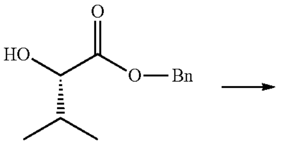

6: L-O-Val-OBn

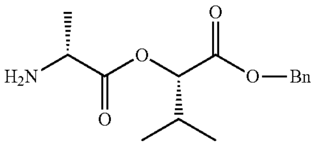

9: R = Boc
10: R = H

Next, the obtained didepsipeptides are bound to synthesize a tetradepsipeptide. At the time, the synthesis can be carried out under any condition as long as it is a condition that can form an amide bond. Preferably, a method of acting various condensing agents under neutral conditions can be adopted. A tetradepsipeptide serves as a repeating unit for cereulide synthesis. For the ease of carrying out the next synthesis, it is also desirable to prepare two types of fragment A and fragment B to which the protective groups are each added to the different portions of the terminals.

[Formula 14]

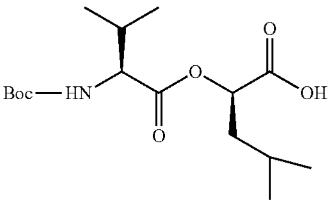

8: Boc-L-Val-D-O-Leu-OH

+

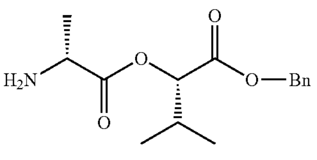

10: H-(D-Ala-L-O-Val)-OBn

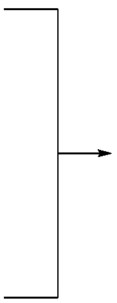

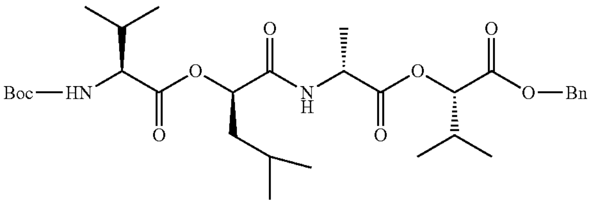

11: Boc-L-Val-D-O-Leu-D-Ala-L-O-Val-OBn

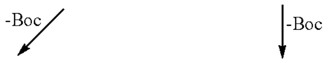

-continued

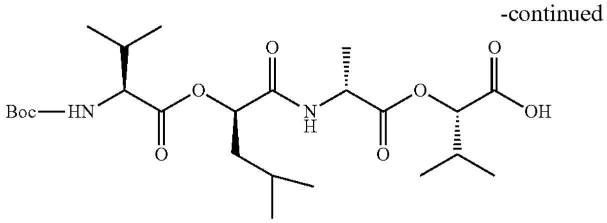

12: Fragment A

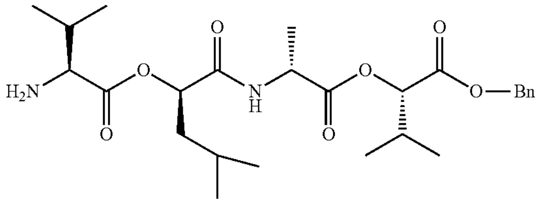

13: Fragment B

The protected repeating structure units that are each a key intermediate of cereulide synthesis, fragment A (12) and fragment B (13), were synthesized in the above pathway.

Furthermore, the fragments obtained as described above are linked by an amide bond, thereby synthesizing an octadepsipeptide and further synthesizing a dodecadepsipeptide.

It is preferred that the linear dodecadepsipeptide obtained as described above be cyclized while preventing an intermolecular reaction, to synthesize cereulide.

[Formula 15]
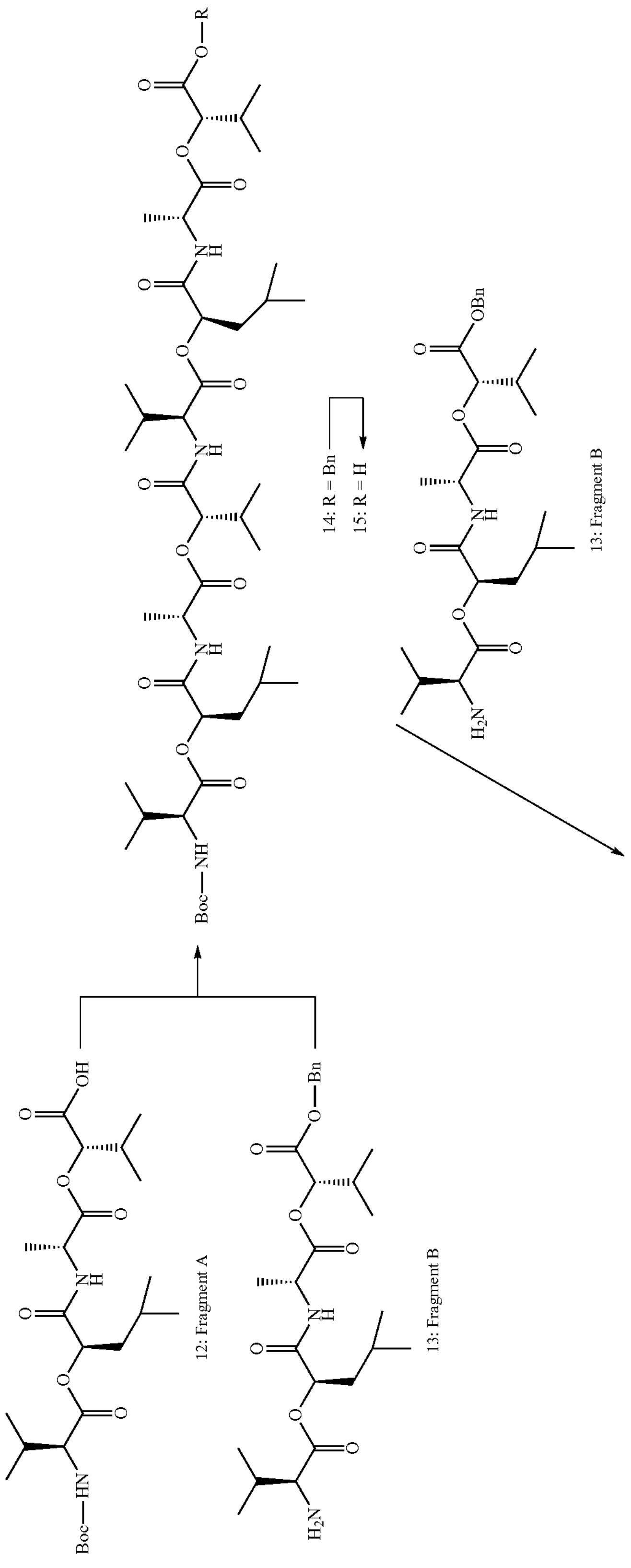
12: Fragment A
13: Fragment B
14: R = Bn
15: R = H
13: Fragment B -continued
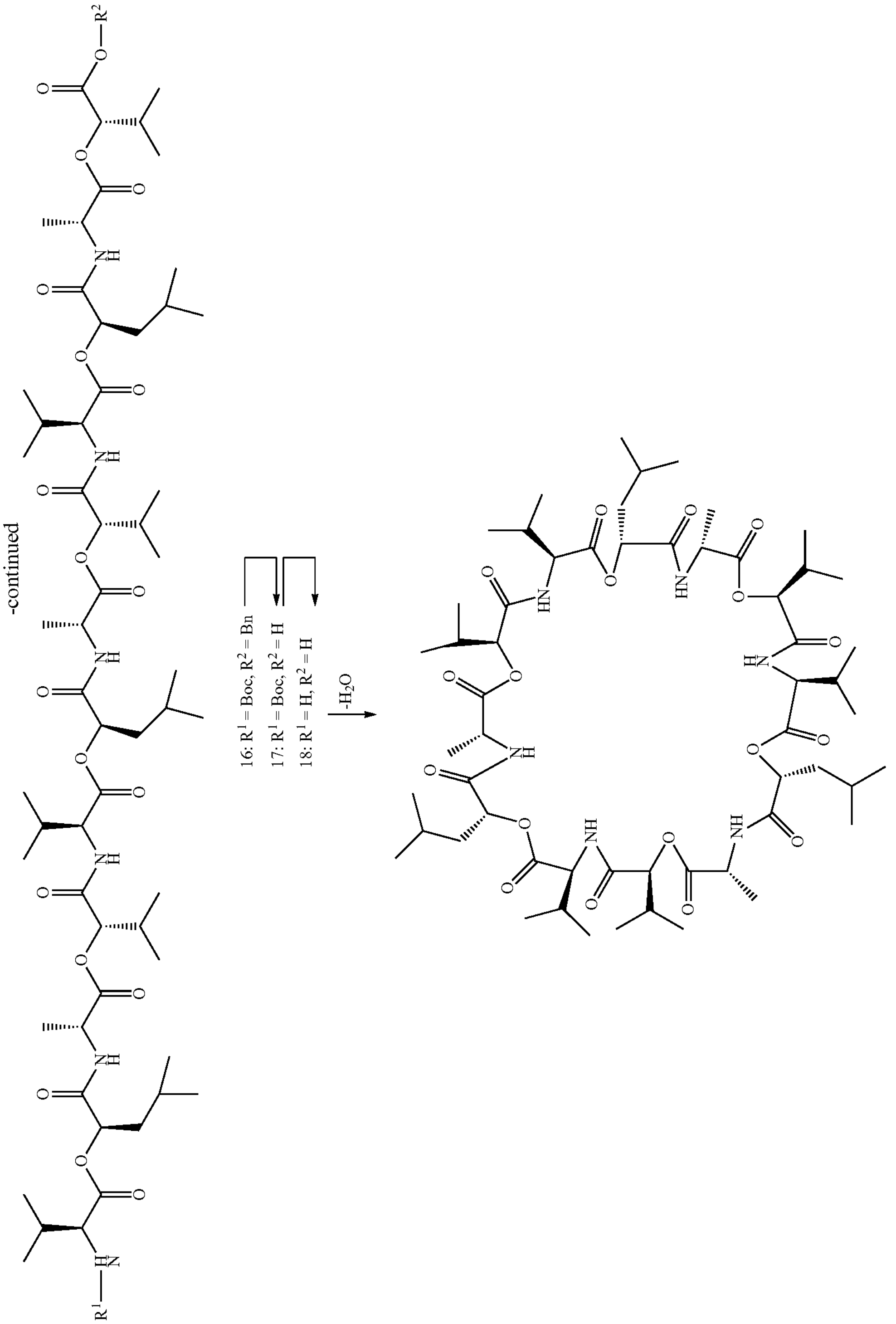
Cereulide In more detail, it is possible to efficiently progress an intramolecular cyclization reaction by optimizing various conditions such as a condensing agent, a solvent and the temperature.

The condensing agent is not limited, but examples include organophosphorous compounds such as diphenylphosphoryl azide (DPPA), diethylphosphoryl cyanidate and azidotris (dimethylamino) phosphonium hexafluorophosphate, quinoline-based peptide condensing agents such as N-ethoxycarbonyl-2-ethoxy-1,2-dihydroquinoline (EEDQ) and 1-isobutyl-2-isobutyl-1,2-dihydroxyquinoline, uronium-based condensing agents such as 0-(7-azabenzotriazol-1-yl)-N,N,N',N'-tetramethyluronium hexafluorophosphate (HATU) and 0-(benzotriazol-1-yl)-N,N,N',N'-tetramethyluronium hexafluorophosphate (HBTU), carbodiimides such as diisopropylcarbodiimide (DIC), dicyclohexylcarbodiimide (DCC) and N-(3-dimethylaminopropyl)-N'-ethylcarbodiimide, and phosphonium-based condensing agents such as (benzotriazole-1-yloxy)tris(dimethylamino)phosphonium hexafluorophosphate, (benzotriazole-1-yloxy)trispyrrolidinophosphonium hexafluorophosphate and bromotripyrrolizinophosphonium hexafluorophosphate. Furthermore, these condensing agents can be used together with an additive such as 1-hydroxy-7-azabenzotriazole (HOAt) or 1-hydroxybenzotriazole (HOBt).

Examples of the solvent used for the reaction include methylene chloride, dimethylformamide and the like.

In the cyclization reaction, an intermolecular bond may be formed in a normal state, and thus it is preferred to perform the cyclization reaction by a high dilution method.

In the present cyclization reaction, the intramolecular reaction precedes an intermolecular reaction, and thus it is possible to increase the yield of isolation of a subject matter. More specifically, it is preferred to suppress the production of a by-product, and precede an intramolecular cyclization reaction.

The present invention further has high applicability in the synthesis of a cereulide derivative (derivative). More specifically, the constituent amino acid or hydroxy acid in the repeating structure unit is appropriately changed, whereby simple synthesis of the derivative is made possible.

For example, novel derivatives such as E-cereulide in which L-valine is replaced by L-glutamic acid, and EAHA-cereulide obtained by introducing aminohexanoic acid into E-cereulide can be synthesized.

These new compounds are expected to be a useful tool molecule for elucidating physiological activity mechanisms of cereulide with many unclear parts, including preparation of an anticereulide antibody.

More specifically, E-cereulide is a derivative in which one L-valine in cereulide is replaced by L-glutamic acid, and EAHA-cereulide is one in which an omega-carboxyl group of E-cereulide is modified with aminohexanoic acid. In these two derivatives, a carboxyl group rich in reactivity is arranged in the external of a 36-membered ring via a carbon chain, and thus, further chemical modification is possible, and these two derivatives can be used as a hapten molecule or labeled molecule for preparing an anticereulide antibody.

[Formula 16]

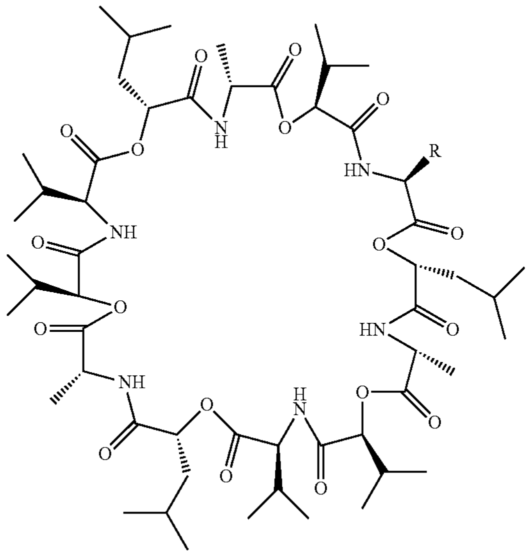

E-Cereulide: R = $(CH_2)_2COOH$
EAHA-Cereulide: R = $(CH_2)_2CONH(CH_2)_5COOH$

Synthesis of such a cereulide derivative can be carried out by preparing one of three tetradepsipeptides L-Val-D-O-Leu-D-Ala-L-O-Val, that is a repeating unit of cereulide, of which L-valine is replaced with L-glutamic acid {R=$(CH_2)_2COOH$} or L-glutamic acid+aminohexanoic acid {R=$(CH_2)_5COOH$}.

That is, it is possible to carry out the synthesis specifically by the following method. For example, the cereulide derivative can be synthesized using a commercially available protective L-glutamic acid derivative or the like as a starting material.

[Formula 17]

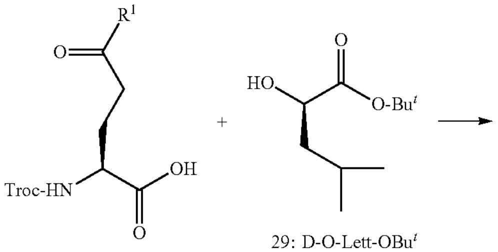

22a, b

29: D-O-Lett-OBu$^t$

Series a ; $R^1$ = OBn
Series b ; $R^1$ = $NH(CH_2)_6COOBn$

-continued

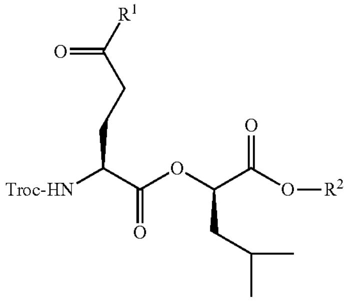

33a, b : $R^2$ = $Bu^t$
34a, b : $R^2$ = H

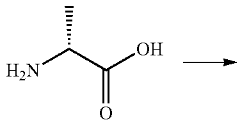

D-Ala

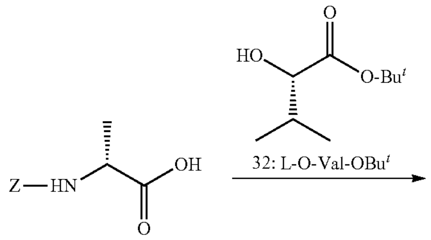

Z-D-Ala

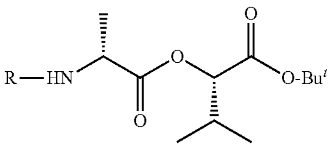

35: R = Z
36: R = H

[Formula 18]

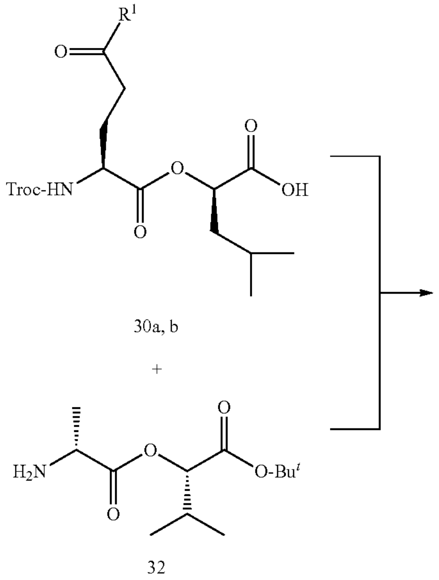

-continued

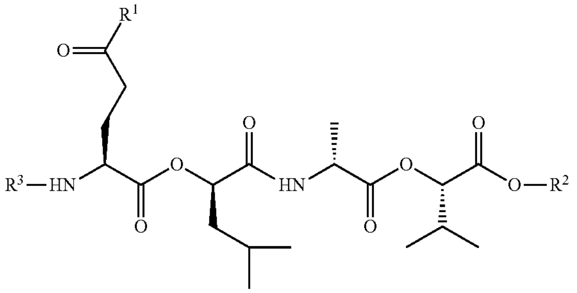

33a, b: $R^2$ = $Bu^t$, $R^3$ = Troc
34a, b: $R^2$ = $Bu^t$, $R^3$ = H

Series a ; $R^1$ = OBn Series b ; $R^1$ = $NH(CH_2)_5COOBn$

A didepsipeptide may be synthesized under any condition as long as it is a condition that can achieve esterification by a dehydration reaction. Particularly preferred is a reaction carried out by adding a strong base such as dimethylaminopyridine and dicyclohexylcarbodiimide to a solvent such as a dichloromethane solution, but it is not limited thereto.

It is preferred to thereafter remove the group protecting the carboxyl group and use it in the subsequent tetradepsipeptide synthesis. Meanwhile, it is possible to bind D-alanine to D-valine acid, then remove the group protecting the amino group and use it in the subsequent tetradepsipeptide synthesis.

The obtained didepsipeptides are bound to synthesize a tetradepsipeptide. The synthesis can be carried out under any condition as long as it is a condition that can form an amide bond. Preferably, a method of acting various condensing agents under neutral conditions can be adopted. For the ease of carrying out the next synthesis, it is desirable to prepare two types of fragment C and fragment D.

Furthermore, the fragments obtained as described above are linked by an amide bond, thereby synthesizing an octadepsipeptide and further synthesizing a dodecadepsipeptide. An example thereof is shown below, but is not limited thereto, and a method of linking tetradepsipeptides, the position of the protective group and the like can be appropriately changed.

[Formula 19]

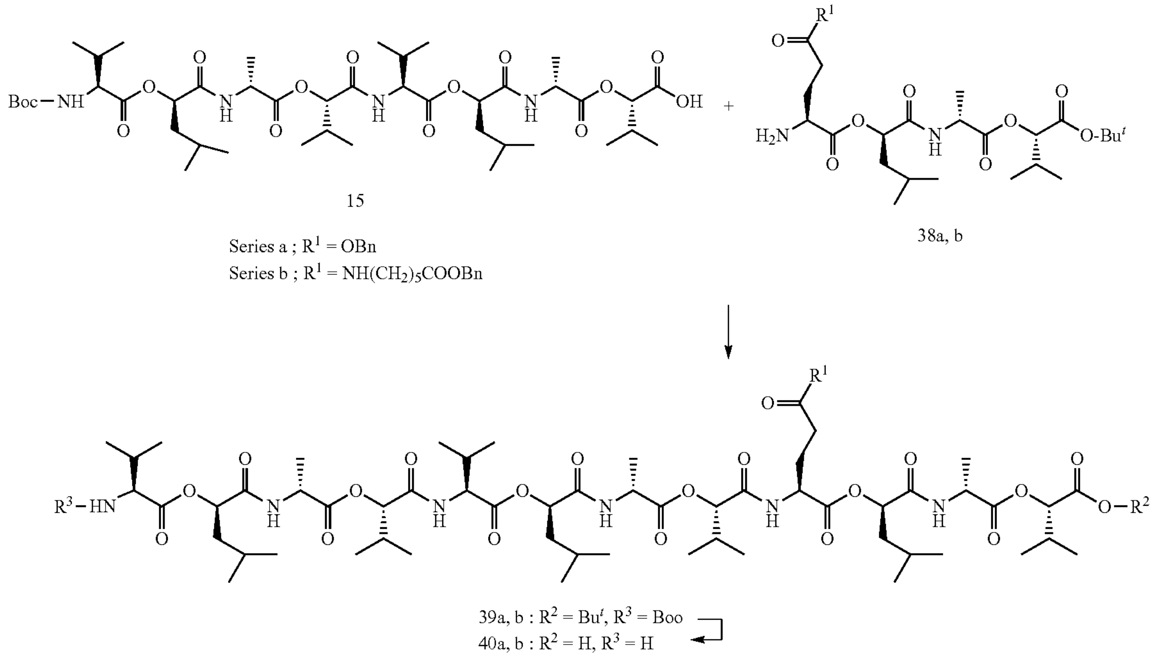

15

Series a ; $R^1$ = OBn
Series b ; $R^1$ = $NH(CH_2)_5COOBn$ 38a, b 39a, b : $R^2$ = $Bu^t$, $R^3$ = Boo
40a, b : $R^2$ = H, $R^3$ = H Here, when synthesizing a depsipeptide, 34a, b having L-glutamic acid (Series a) or L-glutamic acid+amino-hexanoic acid (Series b) may be bound so as to be sandwiched between fragment A and fragment B, and further, the amino group terminal of fragment 5 can also be bound to the carboxyl group terminal of 34a, b, by appropriately changing the position of the protective group.

It is preferred that the linear dodecadepsipeptide obtained as described above be cyclized while preventing an intermolecular reaction, to synthesize a cereulide derivative:

[Formula 20]

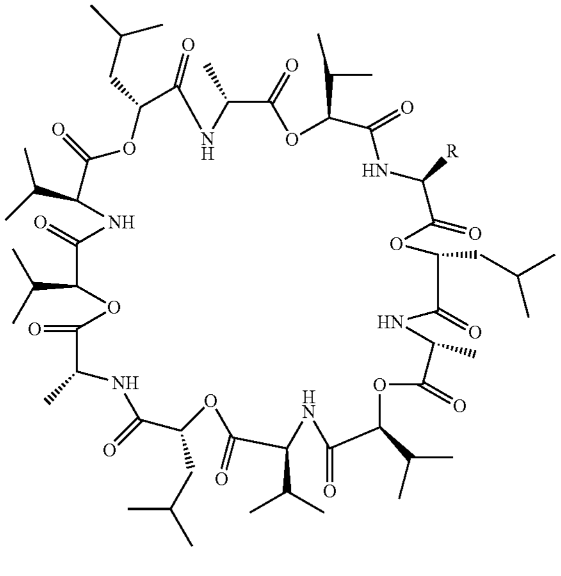

wherein R represents $(CH_2)_2COOH$ or $(CH_2)_2CONH(CH_2)_5COOH$.

The cereulide derivative as described above can be easily modified, and is useful for the production of an antigen for the antibody production. Furthermore, it is also possible to label the cereulide derivative, in order to make a tool for elucidating physiological functions of cereulide.

In order to make an antigen for the antibody production, it is preferred to bind a polymer such as bovine serum albumin (BSA) or keyhole lympet hemocyanin (KLH) to the carboxyl group part of the cereulide derivative.

A labeled cereulide to be a tool for elucidating physiological functions can be achieved, for example, by covalently binding a labeled substance such as biotin to the carboxyl group part of the cereulide derivative.

As a tool for revealing the physiological activity of cereulide at a molecular level, a photolabeled form was synthesized by introducing biotin into the side chain of E-cereulide.

In each step of the synthesis as described above, the substance is properly subjected to a neutralization step and a purification step, and then may be subjected to the next step. Each product in each of the steps as described above may be isolated and purified, or may be directly subjected to the next step. Examples of the isolation and purification means include washing, extraction, a recrystallization method, various chromatographic techniques and the like. Each product in each step can be subjected to any one of these isolation and purification means or any proper combination of two or more kinds of these isolation and purification means.

The cereulide and a derivative thereof obtained in the method of the present invention and a derivative thereof are obtained in a high yield and have high purity, and thus are highly useful as a cereulide specimen. In the present invention, it is also possible to provide a cereulide detection kit containing a cereulide specimen. The cereulide detection kit as described above can be provided with a solvent to dissolve cereulide, a culture medium and the like. Furthermore, cereulide can be widely used for applications such as a potassium ion selective electrode utilizing cereulide's properties of incorporating potassium ion, and an anticancer drug utilizing an apoptosis action to cancer cells. Furthermore, it is also possible to provide more specific cancer cell selectivity by a combination with a drug delivery system or the like.

The cereulide derivative of the present invention can be used as it is or in the form of a pharmaceutically acceptable salt, or in the form of mixture of the cereulide derivative with a pharmaceutically acceptable carrier as a preparation known to a person killed in the art.

Examples of the pharmaceutically acceptable salt include salts of an inorganic base, salts of an organic base, salts of an inorganic acid, salts of an organic acid, salts of a basic or acidic amino acid and the like. Preferred examples of the salt of an inorganic base include alkali metal salts such as sodium salts and potassium salts; alkaline earth metal salts such as calcium salts and magnesium salts; and aluminum salts, ammonium salts and the like. Preferred examples of the salt of an organic base include salts of trimethylamine, triethylamine, pyridine, picoline, ethanolamine, diethanolamine, triethanolamine, dicyclohexylamine, N,N'-dibenzylethylenediamine or the like. Preferred examples of the salt of an inorganic acid include salts of hydrochloric acid, hydrobromic acid, nitric acid, sulfuric acid, phosphoric acid or the like. Preferred examples of the salt of an organic acid include salts of formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid or the like. Preferred examples of the salt of a basic amino acid include salts of arginine, lysine, ornithine or the like, and preferred examples of the salt of an acidic amino acid include salts of aspartic acid, glutamic acid or the like.

Hereinbelow, specific examples of the production of cereulide and derivatives thereof of the present invention are described with reference to embodiments of examples, but the present invention is not limited thereto.

EXAMPLES

In the following examples, analysis and separation and purification of the compound were carried out using the following models and reagents.

NMR spectrum: JEOL Ltd. JMTC-400/54/SS 400 MHz (manufactured by JEOL Ltd.). Unless otherwise stated, a liquid sample was measured as a NaCl film, a solid sample was measured as a KBr pellet, and the absorption wavelength is expressed as $cm^{-1}$ in the sentence.) Also, the chemical shift was expressed as a 8 value.

Melting Point: measured using BUCHI Melting point B-545 (all melting points not corrected).

IR: measured using JASCO FT/IR-460 plus. (Unless otherwise stated, a liquid sample was measured as a NaCl film, a solid sample was measured as a KBr pellet, and the absorption wavelength is expressed as $cm^{-1}$ in the sentence.)

Mass analysis: measured using MALDI-TOF-MS manufactured by BRUKER DALTONICS.

Thin-layer chromatography (TLC): developed using MACHEREY-NAGEL DC-Fertigplatten SIL G-25 UV254 plate and using the following solvent systems. In the text, the solvent systems are expressed as the following symbols.

(A) n-hexane:ethyl acetate=3:1
(B) chloroform:methanol=9:1
(C) chloroform:methanol:acetic acid=85:15:3
(D) chloroform:methanol:triethylamine=90:10:3
(E) toluene:ethyl acetate=1:1
(F) n-hexane:ethyl acetate=1:1

Here, Examples 1 to 5 show the synthesis of the cereulide of the present invention, and Examples 6 to 10 show the synthesis of the cereulide derivative of the present invention.

Example 1

Synthesis of Boc Amino Acids

(1) Boc-L-valine (1)

A commercial (manufactured by Tokyo Chemical Industry Co., Ltd.) product was used without purification.

mp; 78° C.

$[a]_D$−6.5° (c 1.0, AcOH)

(2) Boc-D-alanine (2)

Under ice cooling, D-alanine (11, 8.0 g, 89.8 mmol) was dissolved in an aqueous solution (150 mL) of sodium carbonate (19.1 g, 179.6 mmol), and a THF (20 mL) solution of di-tert-butyl dicarbonate ($Boc_2O$, 21.6 g, 98.8 mmol) was added dropwise thereto. After completion of the dropwise addition, the reaction liquid was returned to room temperature, and continuously stirred overnight. The reaction liquid was transferred to a separating funnel, and excess $Boc_2O$ was removed by diethyl ether extraction. Citric acid was added to the aqueous layer to adjust the pH to 3, and then the mixture was extracted three times with ethyl acetate. The combined organic layer was washed once with a saturated saline solution, and the organic layer was dried over anhydrous $Na_2SO_4$, and concentrated under reduced pressure, and then the concentrated residue was recrystallized from ethyl acetate-hexane to obtain a colorless crystal 2 (15.51 g, 91.3%).

TLC; Rf=0.48 (C)

mp; 83.5° C.

$^1$H-NMR ($CDCl_3$); 1.40-1.45 (12H, m), 4.24-4.38 (1H, m, $\underline{CH}CH_3$), 4.98-5.10 (1H, br s, N$\underline{H}$)

[a]D+25.1 (AcOH, c 2.02, 26.6° C.)

IR; 3378, 2995, 2639, 2569, 1736, 1161

Synthesis of hydroxy acids (3, 5) and benzyl esters thereof (4, 6)

(3) D-O-leucine {(2R)-2-hydroxy-4-methylpentanoic acid} (3)[1)]

Under ice cooling, D-leucine (13.11 g, 100 mmol) was dissolved in 1 N sulfuric acid (150 mL), and an aqueous solution (50 mL) of sodium nitrite (10.35 g, 150 mmol) was added dropwise thereto from a dropping funnel. The reaction liquid was stirred for 3 hours under ice cooling, then further stirred for 6 hours under room temperature, and extracted three times with ethyl acetate. The combined organic layer was washed once with a saturated saline solution, dried over anhydrous sodium sulfate, and concentrated under reduced pressure. The concentrated residue was recrystallized from ethyl acetate-hexane to obtain a colorless crystal D-0-leucine 3 (9.60 g, 72.7%).

TLC; Rf=0.33 (C)

mp; 80.1° C. (lit.[1)]78° C.)

$^1$H-NMR (DMSO); 0.36 (3H, d, J=6.34 Hz, CH(C$\underline{H_2}$)$_2$), 0.38 (3H, d, J=6.34 Hz, CH(C$\underline{H_3}$)$_2$), 0.85-0.98 (2H, m, C$\underline{H_2}$), 1.17-1.32 (1H, m, C$\underline{H}$(CH$_3$)$_2$), 3.43 (1H, dd $J_1$=8.78, $J_2$=4.88, C$\underline{H}$CH$_2$)

$^{13}$C-NMR (DMSO); 21.55, 23.24, 23.97, 42.98, 68.22, 176.41

[a]D+11.7° (MeOH, c 1.03, 22.5° C.) {lit.[1)]+11.8° (MeOH, c 1.03)}

IR; 3424, 2911, 1713

(4) L-O-valine {(2S)-2-hydroxy-3-methylbutanoic acid} (5)

L-O-valine (5) was prepared in the same manner as in the synthesis of 3, using commercially available L-valine as a raw material. More specifically, under ice cooling, an aqueous solution (50 mL) of sodium nitrite (10.35 g, 150 mmol) was added dropwise to a 1 N sulfuric acid (150 mL) solution of L-valine (11.71 g, 100 mmol), and after completion of the dropwise addition, the mixture was stirred for 3 hours under ice cooling, and subsequently for 6 hours under room temperature. The reaction liquid was extracted three times with ethyl acetate, the combined organic layer was washed once with a saturated saline solution, a trace amount of contained sulfuric acid was removed, and the organic layer was dried over anhydrous sodium sulfate, and concentrated under reduced pressure. The concentrated residue was recrystallized from ethyl acetate-hexane to obtain 5 (7.07 g, 59.9%) as a colorless crystal.

TLC; Rf=0.37 (C)

mp; 64.1° C. (lit.[2)]66-68° C.)

$^{1}$H-NMR (DMSO); 0.80 (3H, d, J=3.17 Hz, $CH(CH_3)_2$), 0.87 (3H, d, J=3.17 Hz, $CH(CH_3)_2$), 1.85-1.95 (1H, m, $CH(CH_3)_2$), 3.72 (1H, d, J=4.63 Hz, $CHCH(CH_3)_2$), 5.02 (1H, br, COOH)

$^{13}$C-NMR (DMSO); 16.89, 19.05, 31.55, 74.64, 175.51

$[a]_D$+16.8° ($CHCl_3$, c 1.01, 23.5° C.)+{lit.[2)]; 20° ($CHCl_3$, c 4)}

IR; 3433, 2970, 2186, 1714

(5) D-O-leucine benzyl ester {benzyl (2R)-2-hydroxy-4-methylpentanoate} (4)

A mixture of D-O-leucine (3, 3.36 g, 25.4 mmol), benzyl alcohol (7.9 mL, 76.0 mmol), p-toluenesulfonic acid monohydrate (50 mg, 0.26 mmol) and toluene (100 mL) was heated under reflux in a recovery flask equipped with a Dean-Stark apparatus for 7 hours to remove the generated water by azeotropic separation. After confirming disappearance of the raw material by TLC, the reaction liquid was returned to room temperature, and washed with a saturated aqueous solution of sodium hydrogen carbonate, followed by a saturated saline solution. The organic layer was dried over anhydrous sodium sulfate, and concentrated under reduced pressure with an evaporator. The benzyl alcohol contained in the concentrated residue was distilled away under reduced pressure (8 mHg <), using a glass tube oven (bulb to bulb distillation) apparatus. This residue was purified by silica gel column chromatography (hexane:ethyl acetate=90:10) to obtain a pale yellow oily matter 4 (4.95 g, 80.8%).

TLC; Rf=0.38 (A)

$^{1}$H-NMR ($CDCl_3$); 0.91 (3H, d, J=4.39 Hz, $CH(CH_3)_2$), 0.94 (3H, d, J=4.39 Hz, $CH(CH_3)_2$), 1.56-1.62 (2H, m, d, $CH_2$), 2.60-2.65 (1H, m, OH), 4.18-4.26 (1H, m, $CHCH_2$), 5.19 (2H, ABq, $CH_2Ph$), 7.30-7.40 (5H, m, ArH)

$^{13}$C-NMR ($CDCl_3$); 21.52, 23.21, 24.39, 67.25, 69.15, 128.30, 128.30, 128.52, 128.64, 135.21, 175.71)

$[a]_D$+15.4° ($CHCl_3$, c 1.02, 26.8° C.)

IR; 3475, 2956, 2872, 1736, 1607, 1497, 1140

(6) L-O-valine benzyl ester {benzyl (2S)-2-hydroxy-3-methylbutanoate} (6)

A benzyl ester (6) was synthesized in the same manner as in 4 described above.

A mixture of L-O-valine (5, 3.0 g, 25.4 mmol), benzyl alcohol (7.9 mL, 76.0 mmol), p-toluenesulfonic acid monohydrate (50 mg, 0.26 mmol) and toluene (100 mL) was heated under reflux in a reaction vessel equipped with a Dean-Stark apparatus for 7 hours, and subjected to the same treatment and purification to obtain a pale yellow oily matter 6 (4.57 g, 86.4%).

TLC; Rf=0.44 (A)

$^{1}$H-NMR ($CDCl_3$); 0.83 (3H, d, J=6.09 Hz, $CH(CH_3)_2$), 1.01 (3H, d, J=6.09 Hz, $CH(CH_2)_2$), 2.02-2.14 (1H, m, $CH(CH_3)_2$), 2.69 (1H, d, J=6.09, OH), 4.06-4.11 (1H, m, CHCH), 5.22 (2H, ABq, $CH_2Ph$), 7.31-7.60 (5H, m, ArH)

$^{13}$C-NMR ($CDCl_3$); 15.82, 18.77, 32.14, 67.29, 74.98, 128.41, 128.56, 128.64, 135.16, 174.82

$[a]_D$–9.60° ($CHCl_3$, c 2.19, 26.0° C.)

IR; 3505, 3065, 3034, 2965, 2934, 2876, 1733, 1497, 1460, 1137

Example 2

Synthesis of didepsipeptides (7, 8)

(7) Boc-L-Val-D-O-Leu-OBn (7)

Under ice cooling, dimethylaminopyridine (DMAP, 0.55 g, 4.50 mmol) was added to a dichloromethane (80 mL) solution of D-O-leucine benzyl ester (4, 5.0 g, 22.5 mmol) and commercially available Boc-L-valine (1, 5.38 g, 24.8 mmol), and then N,N'-dicyclohexyl carbodiimide (DCC, 5.86 g, 28.4 mmol) was added thereto. This reaction liquid was stirred under ice cooling overnight, then the by-produced DCurea was removed by suction filtration, and the filtrate was concentrated under reduced pressure. The concentrated residue was dissolved in ethyl acetate and washed with a saturated aqueous solution of sodium hydrogen carbonate, followed by a saturated saline solution, and the organic layer was dried over anhydrous sodium sulfate, and concentrated under reduced pressure. This concentrated residue was purified by silica gel column chromatography (hexane/ethyl acetate) to obtain a colorless solid 7 (9.30 g, 98%).

TLC; Rf=0.56 (A)

$^{1}$H-NMR ($CDCl_3$); 0.78-0.92 (12H, m, $CH(CH_3)_2$), 1.37 (9H, s, tert-Bu), 1.50-1.82 (3H, m), 2.02-2.20 (1H, m, $CH(CH_3)_2$), 4.18-4.32 (1H, m, $CHCH_2CH(CH_3)_2$), 4.91 (1H, d, J=8.78 Hz, NH), 5.04 (1H, dd, $J_1$=10.0 Hz, $J_2$=3.66 Hz), 5.10 (2H, ABq, $CH_2Ph$), 7.28-7.36 (5H, m, ArH)

$^{13}$C-NMR ($CDCl_3$); 17.31, 19.04, 21.27, 23.04, 24.49, 28.30, 31.23, 39.62, 58.62, 67.04, 71.59, 79.72, 128.22, 128.41, 128.59, 135.22, 155.49, 170.12, 171.78

$[a]_D$+15.58° ($CHCl_3$, c 0.40, 16.6° C.)

IR; 3384, 2964, 2875, 1746, 1717, 1501, 1462, 1177

(8) Boc-L-Val-D-O-Leu-OH (8) (Removal of Benzyl Group by Hydrogenolysis)

A flask for hydrogenation was charged with a mixture of Boc-L-Val-D-O-Leu-OBn (7, 2.70 g, 6.40 mmol), methanol (30 mL) and 10% palladium carbon (135 mg), and the mixture was stirred under a hydrogen stream (3 atmospheres) at room temperature for 3 hours. After confirming the progress of the reaction by TLC, the catalyst was removed by filtration, and the filtrate was concentrated under reduced pressure to obtain a colorless solid 8 (2.14 g, quant). This solid was used for the next reaction without further purification.

TLC; Rf=0.55 (C)

mp; 95.8° C.

$^1$H-NMR ($CDCl_3$); 0.86-1.06 (12H, m, $CH(CH_3)_2$), 1.44 (9H, s, tert-Bu), 1.72-1.80 (2H, m, $CH_2CH(CH_3)_2$), 1.80-1.86 (1H, m, $CHCH(CH_3)_2$), 2.14-2.28 (1H, m, $CH_2CH(CH_3)_2$), 4.22-4.33 (1H, m, $CHCH_2$), 5.00-5.06 (1H, m, NH), 5.06-5.14 (1H, m, $CHCH(CH_3)_2$)

$^{13}$C-NMR ($CDCl_3$); 17.49, 19.06, 21.17, 23.06, 24.54, 28.28, 30.93, 39.62, 52.49, 58.86, 69.99, 71.19, 80.19, 113.79, 121.42, 155.84, 174.30

IR; 3516, 3396, 3093, 2961, 2606, 1726, 1520, 1463, 1409, 1178

(9) Boc-D-Ala-L-O-Val-OBn (9)[4)]

A didepsipeptide (9) was synthesized in the same manner as in 7. More specifically, Boc-D-alanine (2, 4.46 g, 23.6 mmol), L-O-valine benzyl ester (6, 4.10 g, 19.7 mmol) and dichloromethane (50 mL) were stirred under ice cooling. DMAP (0.72 g, 5.90 mmol) was added thereto, then DCC (5.07 g, 24.59 mmol) was added thereto, and the mixture was stirred under ice cooling overnight. The by-produced DCurea was removed by suction filtration, the filtrate was concentrated under reduced pressure, and then the concentrated residue was dissolved in ethyl acetate. This ethyl acetate solution was washed with a saturated aqueous solution of sodium hydrogen carbonate, followed by a saturated saline solution, and the organic layer was dried over anhydrous sodium sulfate, and concentrated under reduced pressure. The concentrated residue was purified by silica gel column chromatography (hexane/ethyl acetate) to obtain a colorless solid 9 (7.66 g, quant).

TLC; Rf=0.56 (A)

mp; 63.4° C.

$^1$H-NMR ($CDCl_3$); 0.94 (3H, d, J=6.83 Hz, $CH(CH_3)_2$), 0.98 (3H, d, J=6.83 Hz, $CH(CH_3)_2$), 1.41 (3H, d, J=7.07 Hz, $CHCH_3$), 1.45 (9H, s, tert-Bu), 2.22-2.34 (1H, m, $CH(CH_3)_2$), 4.43-4.50 (1H, m, $CHCH_3$), 4.93 (1H, d, J=4.39, $CHCHCH_3$), 5.03 (1H, br, NH), 5.18 (2H, ABq, $CH_2Ph$), 7.28-7.40 (5H, m, ArH)

$^{13}$C-NMR ($CDCl_3$); 17.01, 18.59, 18.70, 28.31, 30.12, 49.33, 66.97, 79.76, 128.32, 128.43, 135.22, 154.91, 169.06, 172.74

IR; 3396, 2976, 1741, 1688, 1509, 1459, 1161

$[a]_D$−10.70° ($CHCl_3$, c 1.02, 27.0° C.)

(10) $H_2$N-D-Ala-L-O-Val-OBn TFA (10) (Removal of Boc Group)

Under ice cooling, trifluoroacetic acid (TFA, 7.5 mL) was added to a dichloromethane (7.5 mL) solution of Boc-L-Val-D-O-Leu-OBn (9) (2.43 g, 6.40 mmol). This reaction liquid was stirred for 30 minutes under ice cooling, and subsequently for 30 minutes under room temperature. After confirming by TLC that the Boc group was removed, the reaction liquid was concentrated under reduced pressure to obtain a pale yellow oily matter 10 (2.41 g, quant) as a TFA salt. This oily matter was used for the next reaction without further purification.

TLC; Rf=0.51 (B)

$^1$H-NMR ($CDCl_3$); 0.82 (3H, d, J=6.83 Hz, $CH(CH_3)_2$), 0.87 (3H, d, J=6.83 Hz, $CH(CH_3)_2$), 1.54 (3H, d, J=7.32 Hz, $CHCH_3$), 2.12 (1H, m, $CH(CH_3)_2$), 4.12 (1H, q, J=7.32 Hz, $CHCH_3$), 4.91 (1H, d, J=4.15, $CHCH(CH_3)_2$), 5.06 (2H, ABq, $CH_2$ Ph), 7.20-7.30 (5H, m, ArH)

$^{13}$C-NMR ($CDCl_3$); 15.54, 16.77, 18.40, 30.05, 49.01, 67.39, 78.35, 128.45, 128.57, 128.60, 134.96, 168.69, 169.70

IR; 3420, 3035, 2970, 1742, 1674, 1527, 1461, 1141

Example 3

Synthesis of tetradepsipeptide, Fragment A and Fragment B

(11) Boc-L-Val-D-O-Leu-D-Ala-L-O-Val-OBn (11)

Under ice cooling, N,N-diisopropylethylamine (DIPEA, 1.12 mL, 6.43 mmol) was added to an acetonitrile (10 mL) solution of didepsipeptide $H_2$N-D-Ala-L-O-Val-OBn TFA salt (10, 2.41 g, 6.40 mmol) to neutralize the solution, then an acetonitrile solution (5 mL) of Boc-L-Val-D-O-Leu-OH (8, 2.14 g, 6.40 mmol) was added, and subsequently 1-ethyl-3-(3-dimethylaminopropyl)carbodiimide (EDC) hydrochloride (1.35 g, 7.04 mmol) was added. The ice cooling bath was removed, and the reaction liquid was stirred under room temperature overnight, and then the solvent was distilled away under reduced pressure. This residue was dissolved in ethyl acetate, and the organic layer was washed with a 10% aqueous solution of citric acid, a saturated aqueous solution of sodium hydrogen carbonate, followed by a saturated saline solution, dried over anhydrous sodium sulfate, and concentrated under reduced pressure. This residue was purified by silica gel column chromatography (hexane/ethyl acetate) to obtain a colorless oily matter 11 (3.56 g, 94%).

TLC; Rf=0.33 (A)

$^1$H-NMR ($CDCl_3$); 0.84-1.04 (18H, m, $CH(CH_3)_2$), 1.41 (9H, s, tert-Bu), 1.64-1.84 (3H, m), 2.06-2.15 (1H, m, $CHCH(CH_3)_2$), 2.18-2.30 (1H, m, $CH_2CH(CH_3)_2$), 4.06-4.17 (1H, m, $CHCH_3$), 4.52-4.63 (1H, m, $CHCH_2CH(CH_3)_2$), 4.86-4.94 (1H, m, $CHCH(CH_3)_2$), 5.00-5.05 (1H, m, NH), 5.08-5.27 (2H, m, $CH_2Ph$), 5.26-5.34 (1H, m, $CHCH(CH_3)_2$), 7.09-7.14 (1H, br, NH), 7.28-7.38 (5H, m, ArH)

$^{13}$C-NMR ($CDCl_3$); 16.97, 17.24, 18.06, 18.68, 19.17, 21.38, 23.20, 24.33, 28.25, 30.10, 30.44, 34.54, 40.51, 48.53, 59.53, 63.52, 66.96, 72.66, 80.24, 100.55, 128.36, 128.40, 128.55, 135.27, 155.89, 169.11, 169.79, 170.43, 171.77

$[a]_D$+16.03 ($CHCl_3$, c 0.62, 23.5° C.)

IR; 3344, 2968, 2878, 1756, 1681, 1530, 1462, 1056

(12) $H_2$N-L-Val-D-O-Leu-D-Ala-L-O-Val-OBn TFA (12) (Fragment A)

The protected repeating structure unit (11, 2.43 g, 6.40 mmol) was dissolved in dichloromethane (7.5 mL), TFA (7.5 mL) was added under ice cooling, the mixture was stirred for 30 minutes, and then stirred at room temperature for 30 minutes. After confirming completion of the reaction by TLC, the reaction liquid was concentrated under reduced pressure. A small amount of toluene was added to this residue, the mixture was concentrated under reduced pressure, and the remaining TFA was removed by co-evaporation with toluene. This operation was repeated three times to obtain a pale yellow oily matter 12 (2.42 g, quant). This oily matter was used for the next reaction without further purification.

TLC; Rf=0.59 (C)

$^1$H-NMR ($CDCl_3$); 0.88-1.16 (18H, m, CH(C_H_$_3$)$_2$), 1.52 (3H, d, J=7.32 Hz, CHC_H_$_3$), 1.70-1.85 (6H, m), 2.18-2.30 (1H, m, $CH_2$_CH_($CH_3$)$_2$), 2.38-2.51 (1H, m, $CH_2$_CH_($CH_3$)$_2$), 4.09-4.15 (1H, m, _CH_$CH_3$), 4.58-4.67 (1H, m, _CH_$CH_2$CH($CH_3$)$_2$), 4.86-4.94 (1H, m, _CH_CH($CH_3$)$_2$), 5.00-5.05 (1H, m, N_H_), 5.08-5.27 (2H, m, C_H_$_2$Ph), 5.26-5.34 (1H, m, _CH_CH($CH_3$)$_2$), 7.09-7.14 (1H, br, NH), 7.28-7.38 (5H, m, Ar_H_)

$^{13}$C-NMR ($CDCl_3$); 17.04, 17.08, 18.22, 18.35, 18.61, 21.52, 22.98, 24.30, 29.94, 30.14, 40.74, 48.47, 58.90, 67.02, 74.32, 128.32, 128.40, 128.54, 135.16, 168.33, 169.25, 169.40, 172.25

IR; 3221, 2964, 1748, 1675, 1531, 1461, 1156

(13) Boc-L-Val-D-O-Leu-D-Ala-L-O-Val-OH (13) (Fragment B)

A flask for medium-pressure hydrogenation was charged with a mixture of a methanol solution (20 mL) of the protected repeating structure unit (11, 2.70 g, 6.40 mmol) and 10% palladium carbon (135 mg), and the mixture was stirred under a hydrogen stream (3 atmospheres) at room temperature for 4 hours. After confirming the progress of the reaction by TLC, the solvent was distilled away under reduced pressure to obtain a colorless oily matter 13 (2.12 g, quant). This oily matter was used for the next reaction without purification.

TLC; Rf=0.18 (C)

$^1$H-NMR ($CDCl_3$); 0.87-1.04 (18H, m, CH(C_H_$_3$)$_2$), 1.42-1.50 (12H, m), 1.60-1.81 (3H, m), 2.09-2.18 (1H, m, CHC_H_($CH_3$)$_2$), 2.25-2.35 (1H, m, $CH_2$_CH_($CH_3$)$_2$), 4.13-4.23 (1H, m, _CH_$CH_3$), 4.52-4.62 (1H, m, _CH_$CH_2$_CH_($CH_3$)$_2$), 5.04-5.12 (2H, m), 5.32-5.38 (1H, m, _CH_CH($CH_3$)$_2$), 7.34-7.39 (1H, d, J=7.56 Hz, NH)

$^{13}$C-NMR ($CDCl_3$); 16.78, 16.83, 17.87, 18.78, 19.12, 21.20, 23.20, 24.30, 28.21, 29.93, 30.39, 40.60, 48.28, 59.40, 72.80, 77.21, 80.64, 156.33, 170.45, 171.82, 171.94

IR; 3341, 2968, 2882, 1748, 1688, 1531, 1464, 1371, 1249, 1162, 1057, 1016, 757

Example 4

Synthesis of octadepsipeptide and dodecadepsipeptide

(14) Boc-(L-Val-D-O-Leu-D-Ala-L-O-Val)$_2$-OBn (14)

Under ice cooling, N,N-diisopropylethylamine (DIPEA, 1.03 mL, 5.91 mmol) was added to an acetonitrile (15 mL) solution of fragment A TFA salt (12, 1.75 g, 3.0 mmol), and an acetonitrile (5 mL) solution of fragment B (13, 1.49 g, 3.0 mmol), 0-benzotriazole-N,N,N',N'-tetramethyluronium hexafluorophosphate (HBTU, 1.41 g, 3.71 mmol) and 1-hydroxybenzotriazole (HOBt, 0.40 g, 3.0 mmol) were subsequently added. The reaction liquid was returned to room temperature and stirred overnight, and then the solvent was distilled away under reduced pressure. This residue was dissolved in ethyl acetate, and the ethyl acetate layer was sequentially washed with a 10% aqueous solution of citric acid, saturated sodium hydrogen carbonate and a saturated saline solution, and dried over anhydrous sodium sulfate. The resulting substance was concentrated under reduced pressure, and the residue was purified by silica gel column chromatography (hexane/ethyl acetate) to obtain a colorless solid 14 (2.90 g, quant).

TLC; Rf=0.14 (A)

mp; 57 to 59° C.

$^1$H-NMR ($CDCl_3$); 0.84-1.07 (36H, m), 1.43 (9H, s), 1.47 (3H, d, J=7.56 Hz), 1.49 (3H, d, J=7.32 Hz), 1.65-1.84 (6H, m), 1.97-2.05 (1H, m), 2.29-2.37 (1H, m), 2.37-2.38 (1H, m), 3.88 (3H, t, J=6.59 Hz), 4.08-4.13 (1H, m), 4.38 (1H, t, J=7.81 Hz), 4.58-4.63 (1H, m), 4.85 (1H, d, J=4.39 Hz), 5.03 (1H, d, J=5.85 Hz), 5.09-5.20 (4H, m), 5.37 (1H, dd, J=3.17, 10.0 Hz), 5.04-5.12 (2H, m), 7.30-7.37 (5H, m), 7.68 (1H, d, J=7.32 Hz), 7.68 (1H, d, J=7.32 Hz), 7.68 (1H, d, J=6.10 Hz)

$^{13}$C-NMR ($CDCl_3$); 14.17, 16.43, 16.97, 17.51, 18.64, 18.93, 18.98, 19.31, 19.45, 20.80, 21.05, 21.10, 23.14, 23.36, 24.22, 24.34, 28.22, 29.82, 30.04, 30.09, 40.35, 40.99, 48.25, 49.52, 58.74, 60.34, 60.39, 66.73, 72.41, 72.73, 77.21, 78.68, 80.93, 128.24, 128.28, 128.49, 135.36, 156.45, 169.12, 170.00, 170.42, 170.67, 171.65, 171.91, 172.44

IR; 3319, 2966, 2876, 1751, 1656, 1537, 1463, 1185

$[a]_D$+12.7° ($CHCl_3$, c 1.01, 26.5° C.)

(15) Boc-(L-Val-D-O-Leu-D-Ala-L-O-Val)$_2$-OH (15)

A flask for hydrogenation was charged with a mixture of the protected octadepsipeptide 14 (1.00 g, 1.02 mmol), methanol (30 mL) and 10% palladium carbon (50 mg), and the mixture was stirred under a hydrogen stream (3 atmospheres) at room temperature for 4 hours. After confirming the progress of the reaction by TLC, the palladium catalyst was removed by filtration and concentrated under reduced pressure to obtain a colorless oily matter 15 (0.88 g, 97%). This oily matter was used for the next reaction without purification.

TLC; Rf=0.67 (C)

mp; 85 to 87° C.

$^1$H-NMR ($CDCl_3$); 0.80-1.06 (36H, m), 1.43 (9H, s), 1.47 (3H, d, J=7.07 Hz), 1.52 (3H, d, J=7.07 Hz), 1.62-1.84 (6H, m), 1.96-2.08 (1H, m), 2.19-2.38 (3H, m), 3.93 (1H, t, J=6.83 Hz), 4.12-4.22 (1H, m), 4.22-4.31 (1H, m), 4.44-4.61 (1H, m), 4.94-5.02 (2H, m), 5.09 (1H, d, J=6.09 Hz), 7.65 (1H, d, J=6.83 Hz), 7.74 (1H, d, J=5.85 Hz), 7.83 (1H, d, J=7.32 Hz)

The spectrum is shown in FIG. 1.

$^{13}$C-NMR ($CDCl_3$); 16.28, 16.65, 16.87, 18.74, 19.01, 19.21, 19.26, 21.04, 23.22, 23.26, 24.35, 28.23, 29.53, 29.93, 30.18, 30.35, 40.41, 40.65, 48.00, 49.37, 59.28, 60.12, 72.69, 77.21, 78.82, 80.84, 156.46, 170.62, 170.71, 170.88, 171.12, 171.22, 171.53, 171.75, 172.33

IR; 3060, 2966, 2876, 1751, 1658, 1535, 1465, 1389, 1370, 1301, 1241, 1155, 1058, 1010, 931, 877, 838, 782, 628

(16) Boc-L-Val-D-O-Leu-D-Ala-L-O-Val)$_3$-OBn (16)

Under ice cooling, an acetonitrile (5 mL) solution of fragment B (13) TFA salt (479 mg, 0.81 mmol) was charged, and neutralized by adding DIPEA (0.14 mL, 0.81 mmol), and then an acetonitrile (5 mL) solution of octadepsipeptide 15 (720 mg, 0.81 mmol) was added. Subsequently, 0-(7-azabenzotriazole-1-yl)-N,N,N',N'-tetramethyluronium hexafluorophosphate (HATU, 334 mg, 0.88 mmol) was added. The reaction liquid was returned to room temperature and stirred overnight, then concentrated under reduced pressure, and the residue was dissolved in ethyl acetate. The ethyl acetate layer was sequentially washed with a 10% aqueous solution of citric acid, a saturated aqueous solution of sodium hydrogen carbonate and a saturated saline solution. The organic layer was dried over anhydrous sodium sulfate, and then concentrated under reduced pressure, and the residue was purified by silica gel column chromatography (hexane/ethyl acetate=7:3) to obtain a colorless solid 16 (905 mg, 82%).

TLC; Rf=0.33 (F)

mp; 71 to 73° C.

Figure 2:
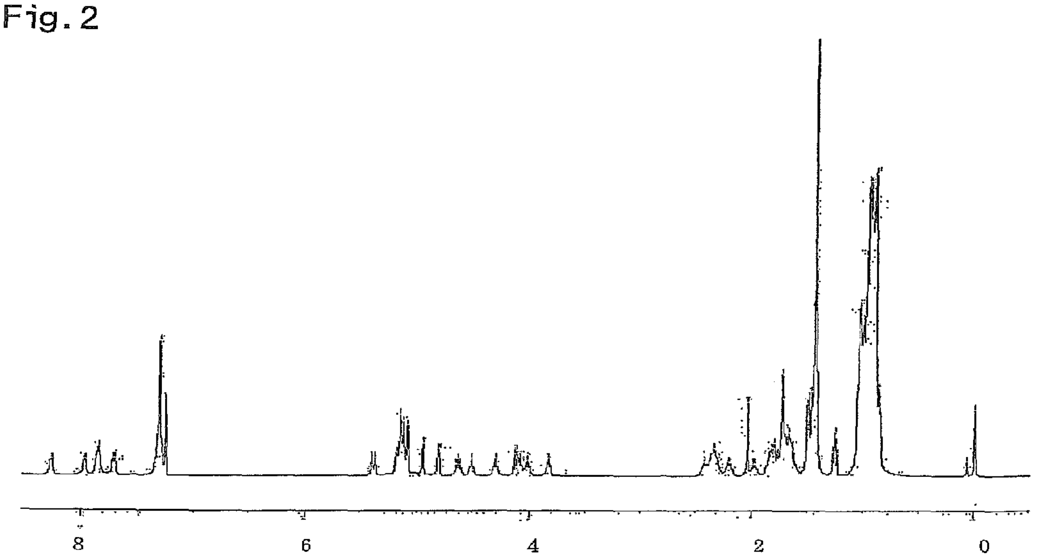
FIG. 2 is a $^1$H-NMR ($CDCl_3$) spectrum of the dodecadepsipeptide of the present invention.

$^1$H-NMR ($CDCl_3$); The spectrum is shown in FIG. 2.

$^{13}$C-NMR ($CDCl_3$); 14.06, 16.27, 16.34, 16.41, 16.53, 17.09, 17.15, 17.68, 18.57, 18.94, 18.98, 19.05, 19.17, 19.20, 19.31, 19.40, 20.69, 20.81, 21.12, 23.03, 23.15, 23.31, 24.20, 24.35, 28.23, 29.74, 30.02, 30.11, 30.15, 30.38, 40.53, 40.90, 41.18, 48.17, 49.36, 49.62, 58.27, 58.73, 60.40, 66.62, 72.41, 72.74, 77.21, 78.88, 79.09, 80.91, 128.20, 128.45, 135.41, 156.56, 169.22, 169.71, 169.96, 170.36, 170.51, 170.56, 170.81, 171.90, 172.45

$[a]_D$+6.12° ($CHCl_3$, c 1.02, 25.9° C.)

IR; 3320, 2965, 2876, 1751, 1655, 1538, 1466, 1370, 1336, 1242, 1184, 1153, 1058, 1006, 933, 876, 747, 697

(17) Boc-(L-Val-D-O-Leu-D-Ala-L-O-Val)$_3$-OH (17)

A reaction vessel for hydrogenation was charged with a mixture of the protected dodecadepsipeptide 16 (133 mg, 97.7 μmol), methanol (5 mL) and 10% palladium carbon (7 mg), and the mixture was stirred under a hydrogen stream (3 atmospheres) at room temperature for 3 hours. After confirming the progress of the reaction by TLC, the solvent was distilled away under reduced pressure to obtain a colorless solid 17 (120.2 mg, 97%). This was used for the next reaction without purification.

TLC; Rf=0.33 (B)

mp; 97 to 99° C.

Figure 3:
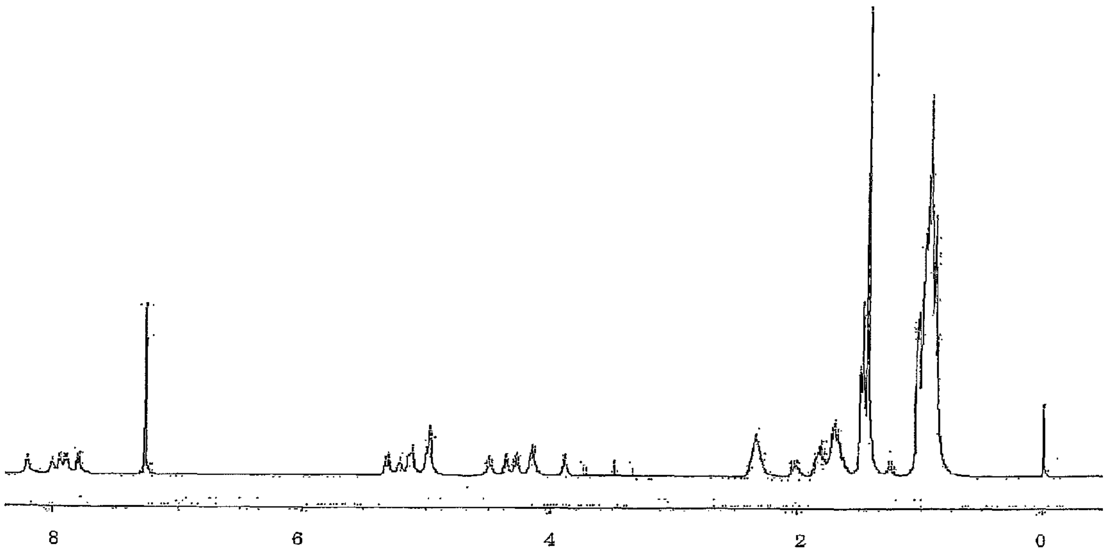
FIG. 3 is a $^1$H-NMR ($CDCl_3$) spectrum of the dodecadepsipeptide of the present invention.

$^1$H-NMR ($CDCl_3$); The spectrum is shown in FIG. 3.

$^{13}$C-NMR ($CDCl_3$); 16.33, 16.39, 16.48, 16.60, 16.78, 16.88, 18.78, 18.84, 18.94, 19.03, 19.18, 19.24, 19.26, 19.31, 20.92, 21.09, 23.18, 23.34, 24.32, 24.39, 28.28, 29.51, 29.86, 29.92, 30.21, 30.22, 40.52, 40.82, 48.26, 49.35, 49.54, 58.82, 59.06, 60.30, 72.77, 72.82, 73.02, 77.23, 77.58, 78.99, 79.04, 80.89, 156.55, 170.46, 170.65, 170.84, 170.97, 171.21, 171.55, 172.11, 172.36, 172.53

IR; 3319, 3068, 2965, 2938, 2876, 1751, 1658, 1536, 1467, 1389, 1370, 1335, 1308, 1249, 1185, 1154, 1128, 1109, 1058, 1008, 933, 877, 755

(18) H-(L-Val-D-O-Leu-D-Ala-L-O-Val)$_3$-OH (18) TFA Salt

Under ice cooling, TFA (2 mL) was added to a dichloromethane (2 mL) solution of 17 (181 mg, 142 μmol), and the mixture was continuously stirred under ice cooling for 1 hour. After confirming the progress of the reaction by TLC, toluene was added to the reaction liquid, and the mixture was concentrated under reduced pressure. In order to completely remove TFA, toluene was added to the concentrated residue and TFA was azeotropically distilled away. This operation was repeated three times to obtain a colorless solid 18 (181 mg, quant). This solid was used for the next cyclization reaction without purification.

TLC; Rf=0.45 (B)

mp; 118 to 121° C.

Figure 4:
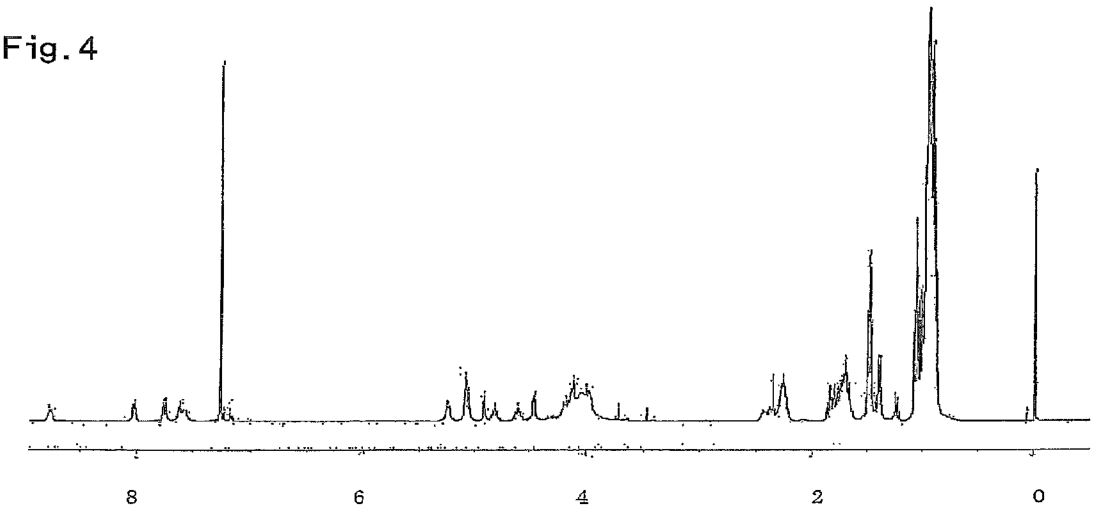
FIG. 4 is a $^1$H-NMR ($CDCl_3$) spectrum of the dodecadepsipeptide of the present invention.

$^1$H-NMR ($CDCl_3$); The spectrum is shown in FIG. 4.

IR; 3310, 3060, 2965, 2882, 2360, 1749, 1659, 1542, 1466, 1389, 1208, 1154, 1059, 1007

Example 5

Synthesis of Cereulide (Cyclization Reaction)

(19) Cereulide

In a reaction vessel replaced with argon, diphenylphosphoryl azide (DPPA) (9.8 μL, 45.5 μmol) was dissolved in anhydrous N,N-dimethylformamide (12 mL), and then N,N-diisopropylethylamine (15.7 μL, 90 μmol) was added thereto to prepare a liquid A. Separately, a precursor 18 (40 mg, 31.5 μmol) was dissolved in anhydrous N,N-dimethylformamide (8 mL) to prepare a liquid B. Under room temperature, the liquid B was added dropwise to the liquid A using a microsyringe over 1 hour or more, and continuously stirred under room temperature for 10 days. The reaction liquid was concentrated under reduced pressure to distill N,N-dimethylformamide away, and the residue was dissolved in ethyl acetate, and sequentially washed with a saturated aqueous solution of sodium hydrogen carbonate, 1 N hydrochloric acid and a saturated saline solution. The organic layer was dried over anhydrous sodium sulfate, and concentrated under reduced pressure, and the residue was purified by silica gel column chromatography (hexane/ethyl acetate=7:3) to obtain cereulide (5.2 mg, 14%) as a pale yellow solid. This cereulide was recrystallized from hot n-hexane to obtain pure cereulide as a colorless crystal.

TLC; Rf=0.23 (F)

mp; 200° C. (lit.[5]) 196-199° C.)

$^1$H-NMR ($CDCl_3$); 0.85-1.02 (m, 45H), 1.06 (d, J=6.59 Hz, 9H), 1.46 (d, J=7.07 Hz, 9H), 1.59-1.85 (m, 9H), 2.24-2.39 (m, 6H), 4.10 (dd, J=9.27, 7.81 Hz, 3H), 4.37-4.42 (m, 3H), 5.01 (d, J=3.17 Hz, 3H), 5.32 (dd, J=7.81, 5.12 Hz, 3H), 7.81 (d, J=6.83 Hz, 6H)

Figure 5:
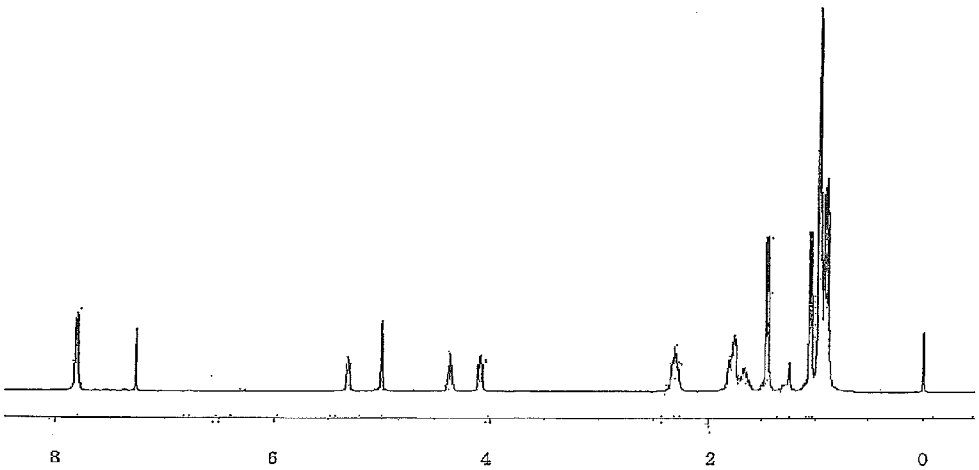
FIG. 5 is a $^1$H-NMR ($CDCl_3$) spectrum of the cereulide of the present invention.

The spectrum is shown in FIG. 5.

$^{13}$C-NMR ($CDCl_3$); 15.75, 16.85, 18.55, 19.28, 21.20, 23.34, 24.37, 28.62, 30.48, 40.54, 48.78, 9.45, 72.69, 78.62, 170.49, 171.07, 171.49, 171.87

$[a]_D$+10.5° C. ($CHCl_3$, c 0.78, 25° C.), {lit.[5])+3.37° ($CHCl_3$, c 1.03)}

IR; 3303, 2963, 2875, 1744, 1656, 1539, 1467, 1246, 1190, 1149, 1057, 1008

MALDI/TOFMS; 1175.576 $[M+Na]^+$, 1191.561 $[M+K]^+$

Example 6

6-Aminohexanoic acid (AHA) and L-glutamic acid derivative (1) 6-Aminohexanoic acid benzyl ester (AHA-OBn, 20) p-TosOH Salt Commercially available 6-aminohexanoic acid (AHA, 19) (6.56 g, 50.0 mmol), benzyl alcohol (15.6 mL, 150 mmol), p-TosOH monohydrate (11.41 g, 60.0 mmol) and toluene (150 mL) were charged in a recovery flask equipped with a Dean-Stark apparatus, and the mixture was heated under reflux for 7 hours to remove the generated water by azeotropic separation. After confirming disappearance of the raw material by TLC, the reaction liquid was returned to room temperature, hexane was added, and then the precipitated crystal was filtered by suction. The crystal was well washed with cold ethyl acetate to obtain a colorless solid 20 (18.71 g, 95.1%).

TLC; Rf=0.35 (D)

mp; 107.9° C.

$^1$H-NMR ($CD_3OD$); 1.29-1.44 (2H, m), 1.54-1.69 (4H, m), 2.33-3.34 (5H, m), 2.80-2.90 (2H, m), 3.26-3.34 (2H, m), 5.11 (2H, s), 7.22 (2H, d, J=7.81), 7.28-7.37 (5H, m), 7.66-7.72 (2H, m)

$^{13}$C-NMR ($CD_3OD$); 21.31, 25.37, 26.79, 28.17, 34.60, 40.50, 67.21, 126.92, 129.92, 129.23, 129.26, 129.55, 129.85, 137.65, 141.75, 143.45, 174.86

IR; 3050, 2945, 2634, 2042, 1730, 1622, 1476, 1248

(2) Troc-L-glutamic acid g-benzyl ester (22a)

Under ice cooling, a commercially available (manufactured by WATANABE CHEMICAL INDUSTRIES, LTD.) L-glutamic acid g-benzyl ester 21 (3.00 g, 12.6 mmol) was dissolved in an aqueous solution (60 mL) of sodium hydrogen carbonate (3.19 g, 38.0 mmol), and a diethyl ether (10 mL) solution of 2,2,2-trichloroethyl chloroformate (Troc-Cl) (2.20 mL, 16.0 mmol) was added dropwise thereto. After completion of the dropwise addition, the reaction liquid was returned to room temperature, and continuously stirred overnight. The reaction liquid was transferred to a separating funnel, and excess Troc-Cl was removed by diethyl ether extraction. The aqueous layer was adjusted to pH 3 by adding citric acid and then extracted three times with ethyl acetate. The combined organic layer was washed once with a saturated saline solution, dried over anhydrous sodium sulfate, and concentrated under reduced pressure, to obtain a colorless oily matter 22a (3.95 g, 75.7%) as the residue. This oily matter was used for the next reaction without purification.

TLC; Rf=0.56 (A)

$^1$H-NMR ($CDCl_3$); 2.07-2.19 (1H, m), 2.18-2.29 (1H, m), 2.31-2.43 (1H, m), 2.46-2.65 (2H, m), 4.54-4.63 (1H, m), 4.66-4.78 (2H, m), 5.14 (2H, s), 5.72 (1H, d, J=8.05 Hz), 7.30-7.40 (5H, m, Ar$\underline{H}$)

IR; 3328, 3035, 2955, 2629, 1732, 1452, 1391, 1214

(3) Troc-L-glutamic acid α-tert-butyl ester (24)

Under ice cooling, a commercially available (manufactured by WATANABE CHEMICAL INDUSTRIES, LTD.) L-glutamic acid tert-butyl ester 23 (1.00 g, 4.92 mmol) was dissolved in an aqueous solution (10 mL) of sodium hydrogen carbonate (827 mg, 9.84 mmol), and a diethyl ether (3 mL) solution of Troc-Cl (0.80 mL, 5.97 mmol) was added dropwise thereto. The reaction treatment was carried out in the same manner as in 22a to obtain a colorless oily matter 24 (1.61 g, 86.4%). This oily matter was used for the next reaction without purification.

TLC; Rf=0.56 (A)

$^1$H-NMR ($CDCl_3$); 1.49 (9H, s), 1.92-2.08 (1H, m), 2.18-2.30 (1H, m), 2.36-2.56 (2H, m), 4.27-4.36 (1H, m), 4.64-4.81 (2H, m), 4.73 (1H, d, J=7.81 Hz)

$^{13}$C-NMR ($CDCl_3$); 27.51, 27.93, 29.79, 53.79, 74.61, 83.03, 95.29, 154.21, 170.52, 178.12

IR; 3336, 2980, 1720, 1528, 1452, 1395, 1370, 1230

(4) Troc-L-glutamic acid (AHA-OBn) α-tert-butyl ester (25)

Under ice cooling, an acetonitrile (7 mL) solution of 20 p-Tos-OH salt (1.83 g, 4.65 mmol) was neutralized by adding DIPEA (1.84 mL, 10.6 mmol), then an acetonitrile solution (3 mL) of 24 (1.60 g, 4.23 mmol) was added thereto, and EDC hydrochloride (972 mg, 5.04 mmol) and HOBt (571 mg, 4.23 mmol) were subsequently added. The ice cooling bath was removed, and the reaction liquid was stirred under room temperature overnight, and then the solvent was distilled away under reduced pressure. This residue was dissolved in ethyl acetate, and the organic layer was washed with a 10% aqueous solution of citric acid, a saturated aqueous solution of sodium hydrogen carbonate and a saturated saline solution, dried over anhydrous sodium sulfate, and concentrated under reduced pressure. This residue was purified by silica gel column chromatography (chloroform) to obtain a colorless oily matter 25 (1.82 g, 74%).

TLC; Rf=0.69 (B)

$^1$H-NMR ($CDCl_3$); $^1$H-NMR ($CDCl_3$); 1.30-1.40 (2H, m), 1.43-1.56 (11H, m), 1.62-1.70 (2H, m), 1.91-2.03 (1H, m), 2.17-2.30 (3H, m), 4.37 (2H, t, J=7.32 Hz), 3.17-3.31 (2H, m), 4.17-4.27 (1H, m), 4.63-4.81 (2H, m), 5.11 (2H, s), 5.90 (1H, d, J=7.56 Hz), 7.31-7.39 (5H, m)

$^{13}$C-NMR ($CDCl_3$); 24.36, 26.25, 27.91, 28.71, 29.06, 32.42, 34.00, 39.31, 54.15, 66.13, 74.54, 82.71, 95.33, 128.16, 128.18, 128.51, 135.91, 154.56, 170.61, 171.68, 173.39

IR; 3322, 3034, 2938, 2867, 1734, 1651, 1537, 1454, 1369, 1229

(5) Troc-L-glutamic acid (AHA-OBn) (22b)

Under ice cooling, trifluoroacetic acid (5.0 mL) was added to a dichloromethane (5.0 mL) solution of 25 (913 mg, 1.57 mmol), and the mixture was stirred for 30 minutes, and subsequently stirred under room temperature for 2.5 hours. After confirming completion of the reaction by TLC, the reaction liquid was concentrated under reduced pressure to obtain a pale yellow oily matter 22b TFA salt (825 mg, quant.). This oily matter was used for the next reaction without purification.

TLC; Rf=0.50 (C)

$^1$H-NMR ($CDCl_3$); 1.30-1.39 (2H, m, $CH_2$), 1.46-1.57 (2H, m, $CH_2$), 1.59-1.70 (2H, m, $C\underline{H_2}$), 2.06-2.14 (1H, m, $\underline{CH}CH_2CH_2CO$), 2.18-2.29 (1H, m, $CH\underline{CH_2}CH_2CO$), 2.34-2.46 (4H, m, $CH_2$), 3.20-3.30 (2H, m, $CH_2$), 4.32-4.39 (1H, m, $\underline{CH}CH_2CH_2CO$), 4.64-4.90 (2H, m, $\underline{CH_2}CCl_3$), 5.12 (2H, s, $\underline{CH_2}Ph$), 6.28 (1H, d, J=7.32, NH), 6.36-6.41 (1H, m, NH), 7.30-7.40 (5H, m, Ar$\underline{H}$)

$^{13}$C-NMR ($CDCl_3$); 24.24, 26.15, 28.68, 28.99, 32.43, 33.98, 39.71, 54.43, 66.35, 74.65, 95.32, 128.22, 128.30, 128.60, 135.88, 154.52, 172.92, 173.73, 173.76

$[a]_D$+8.57° ($CHCl_3$, c 0.46, 16.4° C.)

IR; 3341, 2942, 2602, 1733, 1626, 1541, 1450, 1230, 736

D-Leucine acid and D-valine acid tert-butyl esters (6) D-OAc-leucine {(2R)-2-acetoxy-4-methylpentanoic acid} (27)

Under ice cooling, acetyl chloride (13.4 mL, 154 mmol) was added to D-O-leucine 26 (3, 3.36 g, 25.4 mmol) using a dropping funnel. After confirming disappearance of the raw material by TLC, the reaction liquid was concentrated under reduced pressure. In order to completely remove acetyl chloride in this concentrated residue, operation of co-evaporation with a small amount of toluene was repeated three times to obtain a colorless oily matter 27 (6.52 g, quant.). This oily matter was used for the reaction without purification.

TLC; Rf=0.61 (C)

$^1$H-NMR ($CDCl_3$); 0.94 (3H, d, J=6.34, $CH(\underline{CH_3})_2$), 0.97 (3H, d, J=6.34, $CH(\underline{CH_3})_2$) 1.64-1.72 (1H, m, $\underline{CH}(CH_3)_2$), 1.75-1.86 (2H, m, $\underline{CH_2}CH(CH_3)_2$), 2.15 (3H, s, $CO\underline{CH_3}$), 5.01-5.07 (1H, m, $\underline{CH}CH_2$)

$^{13}$C-NMR ($CDCl_3$); 20.53, 21.41, 22.91, 24.57, 39.50, 70.55, 170.79, 176.70

(7) D-OAc-leucine tert-butyl ester {tert-butyl (2R)-2-acetoxy-4-methylpentanoate} (28)

Under room temperature, DMAP (0.92 g, 7.53 mmol) was slowly added to a mixture of 27 (6.52 g, 37.4 mmol), tert-butanol (40 mL) and $Boc_2O$ (8.26 g, 37.8 mmol). After stirring the mixture for 5 hours at room temperature, the reaction liquid was concentrated under reduced pressure, and the concentrated residue was purified by silica gel column chromatography (hexane/ethyl acetate) to obtain a colorless oily matter 28 (6.56 g, 70.1%).

TLC; Rf=0.54 (A)

$^1$H-NMR ($CDCl_3$); 0.92 (3H, d, J=6.83, $CH(\underline{CH_3})_2$), 0.96 (3H, d, J=6.58 Hz, $CH(\underline{CH_3})_2$), 1.46 (9H, s, <u>tert-Bu</u>), 1.55-1.64 (1H, m, $\underline{CH}(CH_3)_2$), 1.69-1.82 (2H, m, $\underline{CH_2}CH(CH_3)_2$), 2.12 (3H, s, $CO\underline{CH_3}$), 4.85-4.92 (1H, m, $\underline{CH}CH_2$)

$^{13}$C-NMR ($CDCl_3$); 20.70, 21.56, 22.99, 24.62, 27.91, 39.71, 71.52, 81.89, 169.94, 170.64

IR; 2963, 2875, 1746, 1465, 1372

(8) D-O-leucine tert-butyl ester {tert-butyl (2R)-2-hydroxy-4-methylpentanoate} (29)

An aqueous solution (60 mL) of potassium carbonate (19.68 g, 142.4 mmol) was added to a methanol (30 mL) solution of D-OAc-leucine tert-butyl ester (6.56 g, 28.5 mmol), and the mixture was vigorously stirred at room temperature for one day. After completion of the reaction, methanol was distilled away under reduced pressure, and the residue was transferred to a separating funnel and extracted three times with diethyl ether. The combined organic layer was washed with a saturated saline solution, then dried over anhydrous sodium sulfate, and concentrated under reduced pressure, to obtain a colorless oily matter D-O-leucine tert-butyl ester (4.35 g, 81.1%). This oily matter was used for the next reaction without purification.

TLC; Rf=0.52 (A)

$^1$H-NMR ($CDCl_3$); 0.94 (3H, d, J=2.68 Hz, $CH(C\underline{H_3})_2$), 0.96 (3H, d, J=2.44 Hz, $CH(C\underline{H_3})_2$), 1.49-1.53 (11H, m, <u>tert-Bu</u> and $CH\underline{CH_2}CH$), 1.81-1.95 (1H, m, $\underline{CH}(CH_3)_2$), 2.74 (1H, d, J=5.85 Hz, $O\underline{H}$), 4.00-4.09 (1H, m, $\underline{CH}CH_2(CH_3)_2$)

$^{13}$C-NMR ($CDCl_3$); 21.59, 23.32, 24.49, 27.99, 43.59, 69.20, 82.23, 175.23

$[a]_D$−6.90° ($CHCl_3$, c 1.06, 14.7° C.)

IR; 3493, 2959, 2873, 1729, 1465, 1273

(9) L-OAc-valine {(2R)-2-acetoxy-4-methylpentanoic acid} (30)

L-OAc-valine was synthesized in the same manner as that for D-OAc-leucine. More specifically, acetyl chloride (15.0 mL, 211 mmol) was added from a dropping funnel to L-O-valine 5 (5.00 g, 42.3 mmol) under ice cooling. After confirming disappearance of the raw material by TLC, the reaction liquid was concentrated under reduced pressure. A small amount of toluene was added to this residue, the mixture was concentrated under reduced pressure, and the remaining acetyl chloride was removed by co-evaporation with toluene. This operation was repeated three times to obtain a colorless oily matter 30 (6.73 g, quant) as a concentrated residue. This oily matter was used for the next reaction without purification.

TLC; Rf=0.63 (C)

$^1$H-NMR ($CDCl_3$); 1.00-1.06 (6H, m, $CH(C\underline{H_3})_2$), 2.16 (3H, s, $\underline{CH_3}CO$), 2.20-2.33 (1H, m, $\underline{CH}(CH_3)_2$), 4.89 (1H, d, J=4.39 Hz, $\underline{CH}CH(CH_3)_2$), 10.64 (1H, br, COOH)

$^{13}$C-NMR ($CDCl_3$); 17.03, 18.70, 20.48, 29.86, 170.92, 175.61

(10) L-OAc-valine tert-butyl ester {tert-butyl (2S)-2-acetoxy-3-methylbutanoate} (31)

L-OAc-valine tert-butyl ester was synthesized in the same manner as that for D-OAc-leucine tert-butyl ester. More specifically, a mixture of L-OAc-valine (6.73 g, 42.0 mmol), tert-butanol (40 mL) and $Boc_2O$ (9.17 g, 42.0 mmol) was stirred under room temperature, and DMAP (1.03 g, 8.43 mmol) was slowly added thereto. After stirring the mixture at room temperature for 2 hours, the reaction liquid was concentrated under reduced pressure, and the concentrated residue was purified by silica gel column chromatography (hexane/ethyl acetate) to obtain a colorless oily matter L-OAc-valine tert-butyl ester (6.52 g, 71.8%).

TLC; Rf=0.57 (A)

$^1$H-NMR ($CDCl_3$); 0.95-1.01 (6H, m, $CH(\underline{CH_3})_2$), 1.47 (9H, s, <u>tert-Bu</u>), 2.17 (3H, s, $\underline{CH_3}CO$), 2.16-2.24 (1H, m, $\underline{CH}(CH_3)_2$), 4.72 (1H, d, J=4.39 Hz, $\underline{CH}CH(CH_3)_2$)

$^{13}$C-NMR ($CDCl_3$); 17.12, 18.71, 20.64, 27.96, 29.93, 60.37, 81.83, 168.78, 170.77

R; 2975, 2938, 2880, 1744, 1238

(11) L-O-valine tert-butyl ester {tert-butyl (2S)-2-hydroxy-3-methylbutanoate} (32)

L-O-valine tert-butyl ester was synthesized in the same manner as that for L-O-leucine tert-butyl ester. More specifically, an aqueous solution (60 mL) of potassium carbonate (20.83 g, 151.0 mmol) was added to a methanol (30 mL) solution of L-OAc-valine tert-butyl ester (6.52 g, 30.1 mmol), and the mixture was stirred at room temperature for one day. After completion of the reaction, methanol was distilled away under reduced pressure, and the aqueous layer was extracted three times with diethyl ether. The combined organic layer was washed with a saturated saline solution, then dried over anhydrous sodium sulfate, and concentrated under reduced pressure, to obtain a colorless oily matter L-O-valine tert-butyl ester (3.87 g, 73.7%). This oily matter was used for the next reaction without further purification.

TLC; Rf=0.54 (A)

$^1$H-NMR ($CDCl_3$); 0.86 (3H, d, J=6.83 Hz, $CH(C\underline{H_3})_2$), 1.02 (3H, d, J=7.07 Hz, $CH(C\underline{H_3})_2$), 1.50 (9H, s, <u>tert-Bu</u>), 3.92 (1H, d, J=3.41, $\underline{CH}CH(CH_3)_2$)

$^{13}$C-NMR ($CDCl_3$); 15.72, 18.80, 25.58, 28.02, 32.08, 74.88, 82.31, 174.22

$[a]_D$+3.60° (MeOH, c 1.04, 15.1° C.)

IR; 3518, 2970, 2879, 1726, 1465, 1259

Example 7

Synthesis of didepsipeptides

(12) Troc-L-glutamic acid (OBn/AHA-OBn)-D-O-leucine tert-butyl ester (33)

Under ice cooling, DMAP (0.34 mmol) was slowly added to a dichloromethane (10 mL) solution of N-protected L-glutamic acid derivative 22 (1.12 mmol) and D-leucine tert-butyl ester 29 (1.35 mmol), and then DCC (1.68 mmol) was slowly added thereto. This reaction liquid was stirred under ice cooling overnight, then the by-produced DCUrea was removed by suction filtration, and the filtrate was concentrated under reduced pressure. This concentrated residue was dissolved in ethyl acetate, and the organic layer was washed with a saturated aqueous solution of sodium hydrogen carbonate, followed by a saturated saline solution, dried over anhydrous sodium sulfate, and concentrated under reduced pressure. The concentrated residue was purified by silica gel column chromatography (hexane/ethyl acetate) to obtain a target didepsipeptide 33.

33a (R=OBn);

Yield; 35%

TLC; Rf=0.60 (F)

$^1$H-NMR ($CDCl_3$); 0.91 (3H, d, J=6.59 Hz), 0.94 (3H, d, J=6.34 Hz), 1.45 (9H, s), 1.57-1.67 (2H, m), 1.70-1.81 (1H, m), 2.04-2.18 (1H, m), 2.28-2.43 (1H, m), 2.47-2.61 (2H, m), 4.51-4.60 (1H, m), 4.67-4.76 (2H, m), 4.89-4.94 (1H, m), 5.13 (2H, s), 5.69 (1H, d, J=8.29 Hz), 7.30-7.40 (5H, m)

$^{13}$C-NMR ($CDCl_3$); 21.40, 23.01, 24.62, 26.97, 27.32, 27.88, 29.99, 39.46, 53.53, 66.59, 72.69, 74.45, 74.62, 82.43, 95.24, 128.22, 128.31, 128.57, 135.62, 154.04, 168.94, 172.38

IR; 3340, 2959, 1739, 1525, 1453, 1389, 1370, 1259, 1206

33b (R=$NH(CH_2)_5COOBn$);

Yield; 93%

TLC; Rf=0.42 (F)

$^1$H-NMR ($CDCl_3$); 0.89-0.95 (6H, m, $CH(C\underline{H}_3)_2$), 1.30-1.40 (2H, m, $CH_2$), 1.46 (9H, s, tert-Bu), 1.47-1.55 (2H, m, $CH_2$), 1.59-1.80 (6H, m), 2.06-2.16 (1H, m, $CH\underline{CH_2}CH_2CO$), 2.28-2.48 (5H, m), 3.16-3.28 (2H, m, $CH_2$), 4.39-4.47 (1H, m, $\underline{CH}CH_2CH(CH_3)_2$), 4.66-4.77 (2H, m, $\underline{CH_2}CCl_3$), 4.90-4.95 (1H, m, NH), 5.11 (2H, s, $CH_2Ph$), 6.07-6.11 (2H, m, NH), 7.33-7.37 (5H, m, Ar$\underline{H}$)

$^{13}$C-NMR ($CDCl_3$); 14.18, 21.05, 21.40, 23.03, 24.41, 24.55, 26.32, 27.90, 28.01, 29.07, 32.23, 34.04, 39.38, 39.57, 54.11, 60.39, 66.17, 72.49, 74.61, 82.57, 95.29, 128.20, 128.54, 129.01, 135.96, 154.37, 169.54, 170.86, 171.97, 173.38

IR; 3322, 2956, 2871, 1741, 1653, 1537, 1239, 735

(13) Troc-L-glutamic acid (OBn/AHA-OBn)-D-O-leucine (34)

Under ice cooling, TFA (3.0 mL) was slowly added to a dichloromethane (3.0 mL) solution of 33 (0.85 mmol), and the mixture was stirred for 30 minutes under ice cooling, and subsequently stirred under room temperature for 1.5 hours. After confirming completion of the reaction by TLC, the reaction liquid was concentrated under reduced pressure to obtain a pale yellow oily matter 34 (quant.). This oily matter was used for the next reaction without purification.

34a (R=OBn)

Yield; quant

TLC; Rf=0.56 (C)

$^1$H-NMR ($CDCl_3$); 0.92 (3H, d, J=6.10 Hz), 0.95 (3H, d, J=6.34 Hz), 1.65-1.78 (2H, m), 1.80-1.91 (1H, m), 2.02-2.16 (1H, m), 2.26-2.38 (1H, m), 2.41-2.60 (2H, m), 4.49-4.58 (1H, m), 4.62-4.78 (2H, m), 5.06-5.12 (1H, m), 5.13 (2H, s), 5.74 (1H, d, J=8.05 Hz), 7.29-7.40 (5H, m)

$^{13}$C-NMR ($CDCl_3$); 21.29, 22.96, 24.62, 27.11, 29.97, 39.34, 53.54, 66.70, 71.61, 74.70, 95.19, 128.26, 128.36, 128.60, 135.55, 154.19, 170.84, 172.50

IR; 3419, 2959, 1736, 1643, 1521, 1452, 1391, 1210, 1099

34b (R=$NH(CH_2)_5COOBn$)

Yield; quant

TLC; Rf=0.52 (C)

$^1$H-NMR ($CDCl_3$); 0.88-0.99 (6H, m, $CH(C\underline{H}_3)_2$), 1.29-1.40 (2H, m, $CH_2$), 1.44-1.56 (2H, m, $CH_2$), 1.60-1.67 (2H, m, $CH_2$), 1.68-1.79 (2H, m, $CH_2$), 1.82-1.88 (1H, m, $\underline{CH}(CH_3)_2$), 2.10-2.19 (1H, m, $CH\underline{CH_2}CH_2CO$), 2.19-2.30 (1H, m, $CH\underline{CH_2}CH_2CO$), 2.35-2.42 (4H, m, $CH_2$), 3.19-3.28 (2H, m, $CH_2$), 4.39-4.47 (1H, m, $\underline{CH}CH_2CH(CH_3)_2$), 4.67-4.77 (2H, m, $\underline{CH_2}CCl_3$), 5.09-5.11 (1H, m, NH), 5.12 (2H, s, $CH_2Ph$), 6.29 (1H, d, J=7.56 Hz, NH), 6.45-6.52 (1H, m, NH), 7.33-7.39 (5H, m, Ar$\underline{H}$), 8.77 (1H, br, COOH)

$^{13}$C-NMR ($CDCl_3$); 21.30, 23.03, 24.34, 24.58, 26.17, 28.01, 28.67, 32.07, 34.05, 39.36, 39.53, 54.08, 66.47, 71.82, 74.64, 95.22, 128.21, 128.31, 128.58, 135.66, 154.56, 170.81, 172.67, 173.18, 174.17

IR; 3351, 3062, 2957, 2871, 1734, 1630, 1539, 1453, 1386, 1211, 1099

(14) Carbobenzyloxy-D-alanine (Z-D-Ala)

Under ice cooling, commercially available D-alanine (6.00 g, 73.5 mmol) was dissolved in an aqueous solution (225 mL) of sodium carbonate (21.45 g, 202 mmol), and a dioxane (60 mL) solution of benzyl chloroformate (Z—Cl) (10.5 mL, 73.5 mmol) was slowly added dropwise thereto. After completion of the dropwise addition, the reaction liquid was returned to room temperature, and continuously stirred overnight. The reaction liquid was transferred to a separating funnel, and excess Z—Cl was removed by diethyl ether extraction. Citric acid was added to the aqueous layer to adjust the pH to 3, and then the mixture was extracted three times with ethyl acetate. The combined organic layer was washed once with a saturated saline solution, and the organic layer was dried over anhydrous sodium sulfate, and concentrated under reduced pressure, and then the concentrated residue was recrystallized by ethyl acetate-hexane to obtain a colorless crystal Z-D-alanine (13.77 g, 91.6%).

TLC; Rf=0.51 (C)

mp; 82.9° C.

$^1$H-NMR ($CDCl_3$); 1.47 (3H, d, J=7.32 Hz, $\underline{CH_3}$), 4.38-4.48 (1H, m, $\underline{CH}CH_3$), 5.13 (2H, s, $\underline{CH_2}Ph$), 5.29 (1H, br, $\underline{NH}$), 7.30-7.38 (5H, m, Ar$\underline{H}$)

$^{13}$C-NMR ($CDCl_3$); 18.36, 49.52, 67.22, 128.10, 128.25, 128.53, 136.05, 155.92, 177.45

IR; 3349, 3046, 1719, 1539, 1252

(15) Z-D-Alanine-L-O-valine tert-butyl ester (35)

Under ice cooling, DMAP (0.35 g, 2.9 mmol) was slowly added to a dichloromethane (30 mL) solution of L-O-valine tert-butyl ester 32 (2.50 g, 14.3 mmol) and Z-D-alanine (3.52 g, 15.8 mmol), and then DCC (3.70 g, 17.9 mmol) was slowly added thereto. This reaction liquid was stirred under ice cooling overnight, then the by-produced DCUrea was removed by suction filtration, and the filtrate was concentrated under reduced pressure. This concentrated residue was dissolved in ethyl acetate, and the organic layer was washed with a saturated aqueous solution of sodium hydrogen carbonate, followed by a saturated saline solution, dried over anhydrous sodium sulfate, and concentrated under reduced pressure. This residue was purified by silica gel column chromatography (hexane/ethyl acetate) to obtain a colorless oily matter 35 (4.26 g, 78.3%).

TLC; Rf=0.36 (A)

$^{1}$H-NMR ($CDCl_3$); 0.92-1.02 (6H, m, $CH(\underline{CH_3})_2$), 1.46 (9H, s, $\underline{tert\text{-}Bu}$), 1.47 (3H, d, J=7.07 Hz, $CH\underline{CH_3}$), 2.18-2.29 (1H, m, $\underline{CH}(CH_3)_2$), 4.46-4.57 (1H, m, $\underline{CH}CH_3$), 4.75 (1H, d, J=4.15 Hz, $\underline{CH}CH(CH_3)_2$), 5.11 (2H, s, $\underline{CH_2}Ph$), 5.35 (1H, d, J=7.07 Hz, $\underline{NH}$), 7.29-7.40 (5H, m, $Ar\underline{H}$)

$^{13}$C-NMR ($CDCl_3$); 16.93, 18.73, 27.93, 30.00, 49.74, 66.84, 82.22, 128.11, 128.13, 128.50, 136.23, 155.46, 168.05, 172.34

IR; 3342, 2974, 2937, 2879, 1734, 1528, 1254

$[a]_D$−18.04° ($CHCl_3$, c 0.875, 15.7° C.)

(16) D-Alanine-L-O-valine tert-butyl ester (36) TFA Salt

A flask for hydrogenation was charged with a mixture of 35 (1.96 g, 5.17 mmol), methanol (30 mL), TFA (0.46 mL, 6.2 mmol) and 10% palladium carbon (100 mg), and the mixture was stirred under a hydrogen stream (3 atmospheres) at room temperature for 3 hours. After confirming the progress of the reaction by TLC, the catalyst was removed by filtration, the filtrate was concentrated under reduced pressure, and the concentrated residue was purified by silica gel column chromatography (chloroform/methanol) to obtain a light brown oily matter 36 (1.65 g, 93.3%).

TLC; Rf=0.34 (B)

$^{1}$H-NMR ($CDCl_3$); 0.96-1.04 (6H, m, $CH(\underline{CH_3})_2$), 1.36 (3H, d, J=8.54 Hz, $CH\underline{CH_3}$), 1.47 (9H, s, $\underline{tert\text{-}Bu}$), 2.20-2.29 (1H, m, $\underline{CH}(CH_3)_2$), 3.66 (1H, q, J=7.07 Hz, $\underline{CH}CH_3$), 4.76 (1H, d, J=4.39 Hz, $\underline{CH}CH(CH_3)_2$)

$^{13}$C-NMR ($CDCl_3$); 16.99, 18.80, 20.29, 27.97, 28.01, 30.02, 32.07, 49.97, 82.01, 168.52, 176.24

IR; 3445, 2977, 1747, 1677, 1537, 1464, 1432, 1395, 1371, 1330, 1204

Example 8

Synthesis of tetradepsipeptides

(17) Troc-L-glutamic acid (OBn/AHA-OBn)-D-O-leucine-D-alanine-L-O-valine tert-butyl ester (37)

Under ice cooling, an acetonitrile (5 mL) solution of N-terminal protected didepsipeptide 36 TFA salt (289 mg, 0.84 mmol) was neutralized by adding DIPEA (0.15 mL, 0.84 mmol), then an acetonitrile (5 mL) solution of C-terminal protected didepsipeptide 34 (0.84 mmol) was added, and HBTU (352 mg, 0.93 mmol) and HOBt (114 mg, 0.84 mmol) were subsequently added. The reaction liquid was returned to room temperature and stirred overnight, and then the reaction liquid was concentrated under reduced pressure. This concentrated residue was dissolved in ethyl acetate, and the ethyl acetate layer was sequentially washed with a 10% aqueous solution of citric acid, a saturated aqueous solution of sodium hydrogen carbonate and a saturated saline solution, and dried over anhydrous sodium sulfate, and then concentrated under reduced pressure. This residue was purified by silica gel column chromatography (hexane/ethyl acetate) to obtain a pale yellow oily matter 37.

37a (R=OBn)

Yield; 75%

TLC; Rf=0.64 (F)

$^{1}$H-NMR ($CDCl_3$); 0.85-1.00 (12H, m), 1.45 (9H, s), 1.48 (3H, d, J=7.32 Hz), 1.60-1.83 (3H, m), 1.99-2.15 (1H, m), 2.15-2.36 (2H, m), 2.41-2.62 (2H, m), 4.43-4.52 (1H, m), 4.60-4.81 (4H, m), 5.14 (2H, s), 5.27 (1H, dd, J=5.61 Hz, J=7.56 Hz), 5.98 (1H, d, J=7.56 Hz), 6.83 (1H, d, J=7.56 Hz), 7.30-7.40 (5H, m)

$^{13}$C-NMR ($CDCl_3$); 16.88, 17.72, 18.69, 21.42, 23.09, 24.47, 26.52, 27.94, 30.02, 40.50, 47.95, 53.69, 66.73, 73.49, 74.74, 82.33, 95.18, 128.28, 128.38, 128.59, 135.49, 154.50, 168.28, 169.22, 170.47, 171.91, 172.37

IR; 3421, 2964, 1739, 1674, 1538, 1455, 1391, 1370, 1256

37b (R=$NH(CH_2)_5CO_2Bn$)

Yield; 55%

TLC; Rf=0.31 (F)

$^{1}$H-NMR ($CDCl_3$); 0.85-1.00 (12H, m), 1.30-1.40 (2H, m), 1.45 (9H, s), 1.49 (3H, d, J=7.32 Hz), 3.19-3.29 (1H, m), 4.39-4.46 (1H, m), 4.62-4.80 (4H, m), 5.11 (2H, s), 5.23 (1H, dd, J=4.88 Hz, J=9.02 Hz), 6.03-6.11 (1H, m), 6.59 (1H, d, J=7.07 Hz), 7.00 (1H, d, J=7.56 Hz), 7.30-7.40 (5H, m)

$^{13}$C-NMR ($CDCl_3$); 16.89, 17.59, 18.69, 21.39, 23.12, 24.33, 24.41, 26.25, 26.92, 27.92, 28.96, 30.00, 31.97, 33.99, 39.45, 40.46, 48.12, 54.22, 66.17, 73.24, 74.66, 77.68, 82.28, 95.27, 128.17, 128.22, 128.54, 128.55, 135.90, 154.72, 168.24, 169.68, 170.68, 171.96, 172.26, 173.44

IR; 3335, 2962, 1757, 1680, 1538, 1455, 1108, 736

(18) L-Glutamic acid (OBn/AHA-OBn)-D-O-leucine-D-alanine-L-O-valine tert-butyl ester (38)

Zinc (310.6 mg, 4.74 mmol) was added to a 90% acetic acid solution (3 mL) of C- and N-terminal protected tetradepsipeptide 37 (0.24 mmol), and the mixture was stirred at room temperature for one day. After completion of the reaction, a large amount of water was added to the reaction liquid, and the mixture was extracted three times with ethyl acetate. The combined organic layer was washed with water, a saturated aqueous solution of sodium hydrogen carbonate, and a saturated saline solution. The organic layer was dried over anhydrous sodium sulfate, and concentrated under reduced pressure to obtain 38.

38a (R=OBn); Pale Yellow Oily Matter

Yield; quant

TLC; Rf=0.53 (B)

$^{1}$H-NMR ($CDCl_3$); 0.78-1.03 (12H, m), 1.40-1.50 (12H, m), 1.60-1.82 (3H, m), 2.05-2.32 (3H, m), 2.31-2.59 (2H, m), 4.33-4.45 (1H, m), 4.65-4.81 (2H, m), 5.13 (2H, s), 5.18-5.25 (1H, m), 6.57 (1H, d, J=7.56 Hz), 6.88 (1H, d, J=7.32 Hz), 7.29-7.38 (5H, m)

$^{13}$C-NMR ($CDCl_3$); 16.94, 18.20, 18.74, 21.53, 23.13, 24.53, 27.96, 27.97, 30.05, 40.64, 47.72, 55.22, 66.39, 72.93, 77.24, 77.83, 82.38, 126.99, 128.20, 128.57, 135.83, 168.13, 168.97, 169.65, 172.22, 172.89

IR; 3346, 2965, 2938, 2875, 1740, 1679, 1538, 1455, 1391, 1370

38b (R=NH$(CH_2)_5$COOBn); Pale Yellow Amorphous Solid;

Yield; 96%

TLC; Rf=0.42 (C)

$^1$H-NMR ($CDCl_3$); 0.82-1.02 (12H, m), 1.30-1.39 (2H, m), 1.42-1.55 (15H, m), 1.58-1.84 (5H, m), 1.87-1.99 (1H, m), 2.14-2.29 (2H, m), 2.29-2.42 (4H, m), 3.13-3.29 (2H, m), 3.63-3.76 (1H, m), 4.70 (1H, d, J=7.56 Hz), 4.73 (1H, d, J=4.39 Hz), 5.11 (2H, s), 5.23 (1H, dd, J=3.90 Hz, J=9.51 Hz), 6.12-6.24 (1H, m), 7.04 (1H, d, J=7.56 Hz), 7.29-7.38 (5H, m)

$^{13}$C-NMR ($CDCl_3$); 14.16, 16.96, 18.00, 18.69, 21.47, 23.10, 24.42, 24.45, 26.32, 27.90, 29.14, 30.01, 32.42, 34.02, 39.25, 40.64, 47.76, 60.39, 66.14, 73.02, 82.39, 128.17, 128.20, 128.53, 135.91, 168.19, 169.73, 172.15, 172.29, 173.41

IR; 3317, 3068, 2962, 2873, 1739, 1663, 1637, 1545, 1456, 1370, 1163

Example 9

Synthesis of dodecadepsipeptides (precursors)

(19) Boc-L-valine-D-O-leucine-D-alanine-L-O-valine-L-valine-D-O-leucine-D-alanine-L-O-valine-L-glutamic acid (OBn/AHA-OBn)-D-O-leucine-D-alanine-L-O-valine tert-butyl ester (39)

Under ice cooling, an acetonitrile (5 mL) solution of C-terminal protected tetradepsipeptide 38 (0.155 mmol) and N-terminal protected octadepsipeptide 15 (137 mg, 0.155 mmol) was charged, and DIPEA (27.0 μL, 0.155 mmol), HOAt (21.1 mg, 0.155 mmol) and HATU (88.2 mg, 0.232 mmol) were added thereto. The reaction liquid was returned to room temperature and stirred overnight, concentrated under reduced pressure, then the residue was dissolved in ethyl acetate, and the ethyl acetate layer was sequentially washed with a 10% aqueous solution of citric acid, a saturated aqueous solution of sodium hydrogen carbonate and a saturated saline solution. The organic layer was dried over anhydrous sodium sulfate, and then concentrated under reduced pressure, and the residue was purified by silica gel column chromatography (hexane/ethyl acetate=3:2) to obtain a colorless oily matter 39.

39a (R=OBn)

Yield; 40%

TLC; Rf=0.64 (F)

$^1$H-NMR ($CDCl_3$); 0.74-1.09 (48H, m), 1.32-1.53 (27H, m), 1.60-1.86 (9H, m), 1.92-2.04 (1H, m), 2.13-2.26 (2H, m), 2.27-2.44 (4H, m), 2.45-2.52 (2H, m), 3.84 (1H, dd, J=5.85 Hz, J=7.56 Hz), 4.01-4.16 (2H, m), 4.27 (1H, t, J=7.56 Hz), 4.48-4.56 (1H, m), 4.60 (1H, t, J=7.56 Hz), 4.65 (1H, d, J=4.15 Hz), 4.97 (1H, d, J=2.93 Hz), 5.07 (1H, d, J=2.68 Hz), 5.27 (1H, dd, J=3.90 Hz, J=8.87 Hz), 7.28-7.37 (5H, m), 7.74 (1H, d, J=7.32 Hz), 7.87 (1H, d, J=7.32 Hz), 7.96 (1H, d, J=5.85 Hz), 8.10 (1H, d, J=7.81 Hz), 8.25 (1H, d, J=6.10 Hz)

$^{13}$C-NMR ($CDCl_3$); $^{13}$C-NMR ($CDCl_3$); 16.18, 16.34, 16.56, 17.02, 17.57, 18.67, 18.95, 19.00, 19.06, 19.22, 19.30, 20.78, 20.89, 21.17, 23.12, 23.13, 23.36, 24.29, 24.39, 24.42, 26.20, 27.93, 28.26, 29.66, 29.80, 29.98, 30.08, 30.19, 30.41, 40.53, 40.65, 40.76, 48.25, 49.43, 49.63, 52.06, 58.97, 60.40, 66.31, 72.69, 72.75, 73.04, 77.56, 78.65, 79.00, 81.00, 81.79, 128.09, 128.24, 128.47, 135.93, 156.56, 168.44, 169.99, 170.15, 170.44, 170.90, 170.93, 171.92, 172.19, 172.26, 172.44, 172.50

IR; 3316, 2965, 2876, 1748, 1658, 1538, 1460, 1369, 1158

38b (R=NH$(CH_2)_5$COOBn)

Yield; 73.5%

TLC; Rf=0.58 (B)

$^1$H-NMR ($CDCl_3$); 0.82-1.09 (48H, m), 1.39-1.53 (33H, m), 1.53-1.89 (11H, m), 1.93-2.05 (1H, m), 2.10-2.44 (9H, m), 3.09-3.28 (2H, m), 3.84 (1H, dd, J=5.85 Hz, J=7.56 Hz), 4.03-4.19 (2H, m), 4.30 (1H, t, J=7.56 Hz), 4.37-4.48 (1H, m), 4.59-4.67 (2H, m), 4.97 (1H, d, J=3.17 Hz), 5.02 (1H, d, J=2.93 Hz), 5.07-5.15 (4H, m), 5.20-5.30 (1H, m), 6.53 (1H, s), 7.28-7.40 (5H, m), 7.66 (1H, d, J=7.32 Hz), 7.87 (1H, d, J=7.56 Hz), 7.94-8.01 (2H, m), 8.29 (1H, d, J=6.10 Hz)

$^{13}$C-NMR ($CDCl_3$); 16.22, 16.33, 16.52, 17.07, 17.62, 18.63, 18.90, 18.96, 19.05, 19.20, 20.77, 20.85, 21.14, 23.06, 23.11, 23.33, 24.29, 24.37, 24.56, 26.46, 27.46, 27.90, 27.93, 28.24, 29.28, 29.69, 29.78, 29.97, 30.03, 30.16, 32.48, 34.13, 39.36, 40.50, 40.66, 40.75, 48.04, 49.28, 49.63, 52.21, 58.84, 60.39, 66.05, 72.70, 72.77, 73.06, 77.20, 77.54, 77.77, 78.82, 78.98, 80.96, 81.93, 128.13, 128.18, 128.50, 136.03, 156.51, 168.31, 169.85, 170.35, 170.59, 170.86, 170.91, 170.98, 171.87, 172.14, 172.23, 172.47, 173.45

IR; 3319, 2965, 2875, 1748, 1656, 1539, 1460, 1370, 1158, 747

(20) L-Valine-D-O-leucine-D-alanine-L-O-valine-L-valine-D-O-leucine-D-alanine-L-O-valine-L-glutamic acid (OBn/AHA-OBn)-D-O-leucine-D-alanine-L-O-valine (40)

Under ice cooling, TFA (2 mL) was slowly added to a dichloromethane (2 mL) solution of 39 (69 μmol), and the mixture was stirred under ice cooling for 1 hour. After confirming the progress of the reaction by TLC, toluene was added to the reaction liquid, and the mixture was concentrated under reduced pressure. In order to completely remove TFA, toluene was added to the concentrated residue and TFA was azeotropically distilled away. This operation was repeated three times to obtain a pale yellow solid 40. This solid was used for the next cyclization reaction without purification.

40a (R=OBn)

Yield; 94%

TLC; Rf=0.43 (B)

$^1$H-NMR ($CDCl_3$); 0.83-1.09 (48H, m), 1.39 (3H, d, J=7.32 Hz), 1.47 (3H, d, J=7.07 Hz), 1.51 (3H, d, J=7.56 Hz), 1.58-1.84 (9H, m), 2.10-2.41 (9H, m), 4.10-4.25 (2H, m), 4.26-4.38 (2H, m), 4.57-4.66 (1H, m), 4.73-4.79 (1H, m), 4.86 (1H, d, J=3.42 Hz), 4.93 (1H, d, J=2.93 Hz), 5.02 (1H, s), 5.05-5.17 (3H, m), 5.27 (1H, dd, J=4.39 Hz, J=7.56 Hz), 7.31-7.41 (5H, m), 7.64 (2H, d, J=8.54 Hz), 7.74 (1H, d, J=3.17 Hz), 7.77 (1H, d, J=7.81 Hz), 8.32 (1H, d, J=5.61 Hz), 8.64 (1H, d, J=5.85 Hz)

$^{13}$C-NMR ($CDCl_3$); 14.98, 15.63, 16.31, 16.70, 17.05, 17.23, 17.44, 17.71, 18.41, 18.54, 18.66, 18.93, 19.12, 19.58, 20.95, 21.11, 21.62, 22.99, 23.10, 23.16, 23.22, 24.33, 24.48, 24.52, 27.84, 29.66, 30.35, 30.54, 40.03, 40.14, 40.38, 50.09, 53.42, 58.74, 66.56, 73.94, 75.13, 78.02, 79.18, 79.24, 82.03, 128.23, 128.58, 128.95, 135.53, 169.15, 170.45, 171.34, 171.54, 171.82, 171.94, 172.12, 172.36, 173.42

IR; 3296, 3068, 2965, 2870, 1749, 1661, 1543, 1466, 1372, 1202

40b (R=NH($CH_2$)$_5$COOBn)

Yield; quant

TLC; Rf=0.36 (B)

$^1$H-NMR ($CDCl_3$); 0.80-1.09 (48H, m), 1.24-1.33 (11H, m), 1.36-1.42 (4H, m), 1.43-1.52 (3H, m), 1.55 (2H, d, J=7.32 Hz), 1.58-1.88 (9H, m), 2.12-2.40 (9H, m), 3.00-3.14 (2H, m), 3.16-3.30 (1H, m), 3.97 (1H, d, J=4.63 Hz), 4.05 (1H, dd, J=7.07 Hz, J=10.49 Hz), 4.60 (1H, t, J=7.56 Hz), 4.65-4.79 (4H, m), 4.83 (1H, d, J=3.41 Hz), 4.88 (1H, d, J=2.68 Hz), 5.02-5.09 (2H, m), 5.11 (2H, s), 5.33 (1H, dd, J=3.41 Hz, J=9.02 Hz), 6.25 (1H, s), 7.29-7.39 (5H, m), 7.54-7.66 (2H, m), 7.82 (1H, d, J=7.56 Hz), 8.58 (1H, d, J=7.32 Hz), 9.27 (1H, s)

$^{13}$C-NMR ($CDCl_3$); 15.37, 15.74, 16.60, 16.74, 16.86, 17.02, 17.39, 17.84, 18.39, 18.46, 18.86, 19.18, 19.38, 20.99, 21.17, 21.28, 22.94, 23.00, 23.24, 24.38, 24.44, 24.49, 26.29, 28.47, 29.04, 29.60, 29.65, 29.83, 30.53, 32.26, 34.00, 39.60, 40.13, 40.40, 47.67, 49.33, 53.17, 58.71, 66.22, 73.03, 75.19, 77.21, 78.90, 128.18, 128.21, 128.24, 128.55, 129.01, 135.89, 169.18, 170.62, 170.78, 171.03, 171.59, 171.63, 172.24, 172.69, 173.26, 173.46

IR; 3300, 3081, 2965, 2876, 1748, 1657, 1545, 1462, 1374, 1203

Example 10

E-Cereulide and EAHA-Cereulide (Cyclization Reaction)

(22) E-Cereulide-OBn (41a) and EAHA-cereulide-OBn (41b)

A cyclization reaction of a precursor 40 was carried out in the same manner as in cereulide synthesis. More specifically, in a reaction vessel replaced with argon, diphenylphosphoryl azide (DPPA) (9.8 μL, 45.5 μmol) was dissolved in anhydrous N,N-dimethylformamide (12 mL), and then N,N-diisopropylethylamine (15.7 μL, 90 μmol) was slowly added thereto to prepare a liquid A.

Separately, the precursor 40 (31 μmol) was dissolved in anhydrous N,N-dimethylformamide (8 mL) to prepare a liquid B.

Under room temperature, the liquid B was slowly added dropwise to the liquid A using a microsyringe over 1 hour or more, and continuously stirred under room temperature for 10 days. The reaction liquid was concentrated under reduced pressure to distill dichloromethane away, and the residue was dissolved in ethyl acetate, and sequentially washed with a saturated aqueous solution of sodium hydrogen carbonate, 1 N hydrochloric acid and a saturated saline solution. The organic layer was dried over anhydrous sodium sulfate, and concentrated under reduced pressure, and the residue was purified by silica gel column chromatography (hexane/ethyl acetate) to obtain a pale yellow solid 41.

41a (R=OBn)

TLC; Rf=0.69 (F)

$^1$H-NMR ($CDCl_3$); 0.78-1.03 (48H, m), 1.40-1.48 (9H, m), 1.58-1.84 (11H, m), 2.10-2.60 (9H, m), 4.00-4.10 (2H, m), 4.25-4.60 (3H, m), 4.91-5.01 (2H, m), 5.02 (1H, d, J=3.17 Hz), 5.10-5.14 (3H, m), 5.23 (1H, dd, J=3.90 Hz, J=5.37 Hz), 5.26-5.33 (2H, m), 7.31-7.37 (5H, m), 7.62 (1H, d, J=6.59 Hz), 7.74-7.80 (3H, m), 7.84 (1H, d, J=5.85 Hz), 7.96 (1H, d, J=7.56 Hz)

$^{13}$C-NMR ($CDCl_3$); 15.72, 15.80, 16.77, 16.89, 18.46, 18.52, 18.65, 19.26, 19.32, 21.11, 21.20, 21.73, 23.01, 23.32, 24.32, 24.36, 24.51, 28.52, 28.72, 30.28, 30.39, 30.47, 30.57, 40.39, 48.57, 48.79, 49.03, 51.78, 59.41, 59.55, 66.42, 72.58, 72.78, 73.30, 78.47, 78.64, 78.77, 128.20, 128.23, 128.53, 169.92, 170.42, 170.63, 171.02, 171.06, 171.33, 171.43, 171.53, 171.74, 171.84, 172.04, 172.18

IR; 3433, 3310, 2964, 2872, 1742, 1654, 1538, 1463, 1389, 1371, 1198, 1160

$[a]_D$+7.17° ($CHCl_3$, c 1.20, 25° C.)

MALDI/TOFMS; 1295 $[M+Na]^+$, 1311 $[M+K]^+$ 41b (R=NH($CH_2$)$_5$COOBn)

TLC; Rf=0.23 (F)

mp; 64.7° C.

$^1$H-NMR ($CDCl_3$); 0.82-1.01 (42H, m), 1.04 (3H, d, J=6.34 Hz), 1.06 (3H, d, J=6.10 Hz), 1.29-1.39 (2H, m), 1.40-1.54 (11H, m), 1.60-1.72 (6H, m), 1.72-1.82 (4H, m), 1.90-2.00 (1H, m), 2.03-2.14 (2H, m), 2.15-2.42 (9H, m), 3.09-3.19 (1H, m), 3.21-3.33 (1H, m), 4.03-4.12 (2H, m), 4.26-4.40 (2H, m), 4.41-4.53 (2H, m), 4.97 (1H, d, J=3.17 Hz), 5.02-5.05 (2H, m), 5.11 (2H, s), 5.15-5.22 (1H, m), 5.25-5.33 (2H, m), 6.42-6.47 (1H, m), 7.29-7.40 (5H, m), 7.63-7.77 (3H, m), 7.84 (1H, d, J=7.32 Hz), 7.91 (1H, d, J=7.07 Hz)

$^{13}$C-NMR ($CDCl_3$); 15.91, 16.70, 16.99, 18.47, 18.56, 19.07, 19.21, 19.30, 19.35, 21.04, 21.36, 21.50, 23.07, 23.27, 23.34, 24.34, 24.52, 26.41, 28.61, 28.74, 29.29, 30.29, 30.35, 30.49, 32.51, 34.09, 39.34, 40.27, 40.53, 48.31, 48.62, 48.90, 52.38, 59.10, 59.59, 66.11, 72.82, 73.17, 78.20, 78.61, 78.89, 128.16, 128.52, 135.97, 170.31, 170.43, 170.62, 170.89, 171.06, 171.25, 171.53, 171.68, 171.76, 173.36

IR; 3298, 2963, 1744, 1657, 1538, 1461

MALDI/TOFMS; 1409 $[M+Na]^+$, 1425 $[M+K]^+$

(22) E-Cereulide and EAHA-Cereulide (Removal of Benzyl Group by Hydrogenolysis Reaction)

A flask for hydrogenation was charged with a mixture of 41 (20 mg), methanol (5 mL) and 10% palladium carbon (2 mg), and the mixture was stirred under a hydrogen stream (3 atmospheres) at room temperature for 3 hours. After confirming the progress of the reaction by TLC, the catalyst was removed by filtration, and the filtrate was concentrated under reduced pressure to obtain E-cereulide and EAHA-cereulide.

E-Cereulide

Yield; quant

TLC; Rf=0.39 (B)

$^1$H-NMR ($CDCl_3$); 0.78-1.12 (48H, m), 1.40-1.54 (9H, m), 1.60-1.90 (8H, m), 2.06-2.16 (1H, m), 2.17-2.42 (6H, m), 2.42-2.63 (3H, m), 4.06-4.15 (2H, m), 4.25-4.35 (1H, m), 4.35-4.43 (1H, m), 4.43-4.56 (2H, m), 4.70-4.82 (1H, m), 4.92-5.04 (1H, m), 5.13-5.31 (1H, m), 6.82 (1H, s), 7.60-7.92 (6H, m), 5.07 (1H, d, J=3.17 Hz), 5.09-5.15 (1H, m), 5.17-5.25 (1H, m), 5.25-5.33 (1H, m), 7.34 (1H, d, J=5.85 Hz), 7.43-7.50 (1H, m), 7.60-7.82 (4H, m), 8.03 (1H, s)

$^{13}$C-NMR ($CDCl_3$); 16.28, 16.48, 16.65, 16.85, 16.94, 18.52, 18.56, 18.73, 19.05, 19.17, 19.24, 21.08, 21.34, 21.40, 21.52, 23.08, 23.22, 23.29, 24.39, 24.61, 24.64, 27.93, 28.73, 29.70, 30.12, 30.48, 40.44, 40.50, 48.26, 48.46, 48.57, 52.48, 59.42, 72.71, 72.88, 73.57, 77.22, 77.92, 78.22, 78.53, 170.00, 170.11, 170.84, 171.16, 171.22, 171.34, 171.45, 171.54, 171.95

IR; 3435, 3316, 2964, 1742, 1654, 1538, 1466, 1383, 1198

MALDI/TOFMS; 1205 $[M+Na]^+$, 1221 $[M+K]^+$

EAHA-Cereulide

Yield; quant

TLC; Rf=0.32 (B)

$^1$H-NMR ($CDCl_3$); 0.75-1.00 (42H, m), 1.06 (6H, d, J=5.85 Hz), 1.34-1.58 (13H, m), 1.58-1.86 (11H, m), 1.95-2.10 (1H, m), 2.17-2.42 (10H, m), 3.09-3.26 (1H, m), 3.26-3.44 (1H, m), 4.00-4.12 (1H, m), 4.12-4.22 (1H, m), 4.27-4.40 (2H, m), 4.40-4.50 (2H, m), 4.97 (1H, d, J=3.17 Hz), 4.99-5.08 (2H, m), 5.13-5.31 (1H, m), 6.82 (1H, s), 7.60-7.92 (6H, m)

IR; 3304, 2963, 2938, 2875, 1743, 1655, 1539, 1466, 1373, 1197

MALDI/TOFMS; 1319 $[M+Na]^+$, 1335 $[M+K]^+$

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A cereulide derivative represented by the following formula:

[Formula 8]

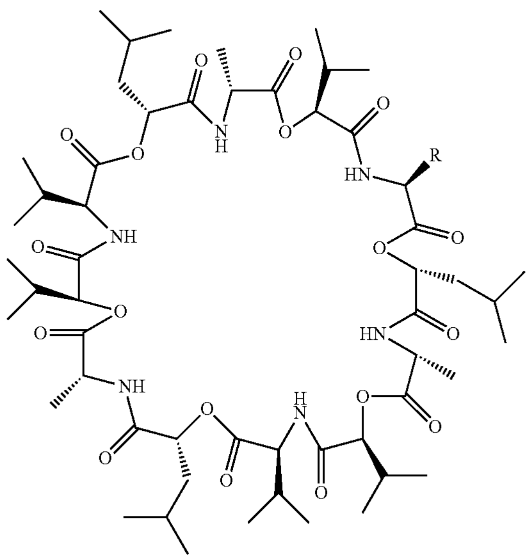

wherein R represents $(CH_2)_2COOH$ or $(CH_2)_2CONH(CH_2)_5COOH$.

2. A precursor of a cereulide derivative, selected from the group consisting of the following formulae:

[Formula 1]

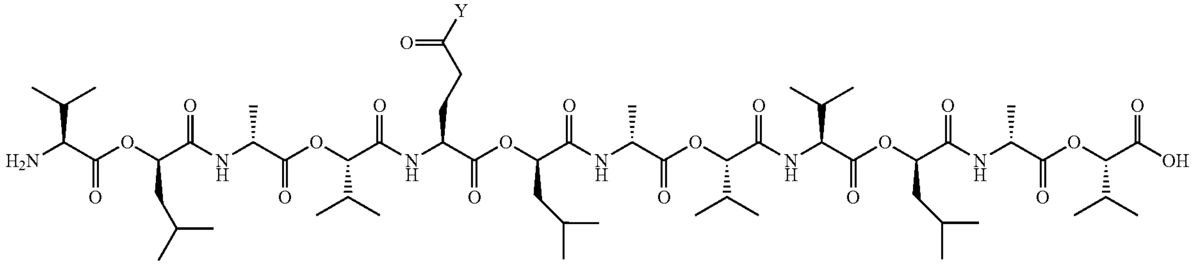

[Formula 2]

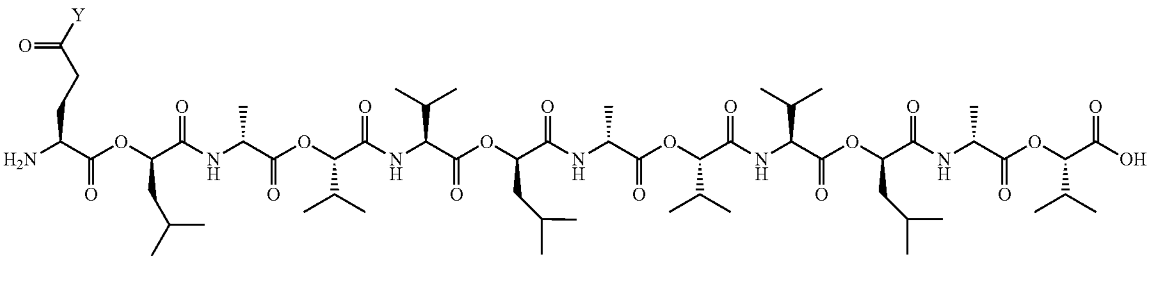

and

-continued

[Formula 3]

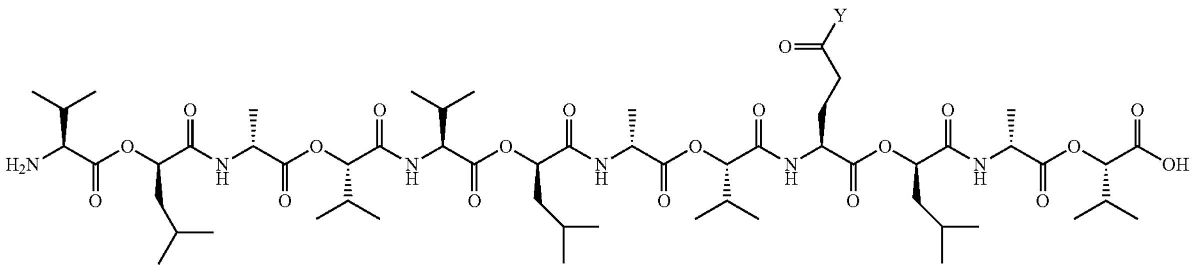

wherein Y represents OH or $NH(CH_2)_5COOH$.

3. A method for producing a cereulide derivative represented by:

[Formula 7]

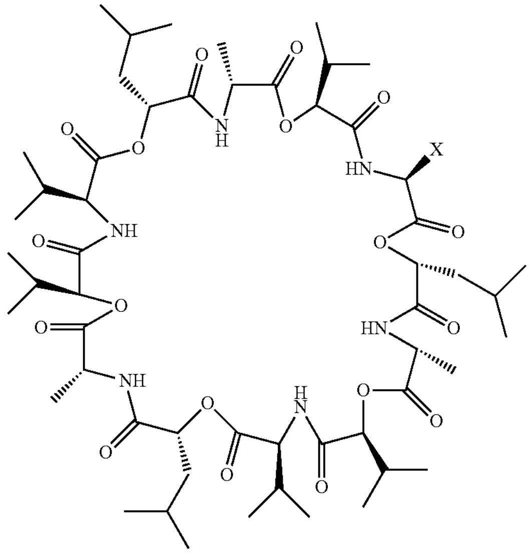

wherein X represents $(CH_2)_2COOH$ or $(CH_2)_2CONH(CH_2)_5COOH$, comprising combining a precursor of a cereulide derivative as defined in claim 2 and a condensing agent in a solvent to perform a cyclization reaction by formation of an intramolecular amide bond of the precursor of a cereulide derivative as defined in claim 2;

wherein the Y group of the cereulide derivative precursor comprises a protecting group; and wherein the method further comprises the step of removing the protecting group after the cyclization reaction.

* * * * *